(12) United States Patent
Hilvert et al.

(10) Patent No.: US 8,653,014 B2
(45) Date of Patent: Feb. 18, 2014

(54) SHAMPOO COMPOSITION CONTAINING A GEL NETWORK

(71) Applicant: The Procter & Gamble Company, Cincinnati, OH (US)

(72) Inventors: Jennifer Elaine Hilvert, Cincinnati, OH (US); Stephanie Marie Harris Riley, Mason, OH (US); Elizabeth Rebecca Aistrup, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/646,227

(22) Filed: Oct. 5, 2012

(65) Prior Publication Data
US 2013/0090279 A1   Apr. 11, 2013

Related U.S. Application Data

(60) Provisional application No. 61/597,292, filed on Feb. 10, 2012, provisional application No. 61/544,750, filed on Oct. 7, 2011, provisional application No. 61/544,769, filed on Oct. 7, 2011, provisional application No. 61/584,515, filed on Jan. 9, 2012.

(51) Int. Cl.
*A61K 8/00* (2006.01)

(52) U.S. Cl.
USPC ........... 510/119; 510/121; 510/123; 510/125; 510/130; 510/424; 510/426

(58) Field of Classification Search
None
See application file for complete search history.

(56) References Cited

U.S. PATENT DOCUMENTS

| | | |
|---|---|---|
| 2,396,278 A | 3/1946 | Lind et al. |
| 2,438,091 A | 3/1948 | Lynch et al. |
| 2,486,921 A | 11/1949 | Byerly et al. |
| 2,486,922 A | 11/1949 | Strain et al. |
| 2,528,378 A | 10/1950 | Manheimer et al. |
| 2,658,072 A | 11/1953 | Kosmin et al. |
| 2,694,668 A | 11/1954 | Pricke et al. |
| 2,786,847 A | 3/1957 | Cislak et al. |
| 2,798,053 A | 7/1957 | Brown et al. |
| 2,809,971 A | 10/1957 | Berstein et al. |
| 2,826,551 A | 3/1958 | Geen et al. |
| 3,152,046 A | 10/1964 | Kapral et al. |
| 3,155,591 A | 11/1964 | Hilfer et al. |
| 2,326,733 A | 2/1966 | Karsten et al. |
| 3,236,733 A | 2/1966 | Karsten et al. |
| 3,332,880 A | 7/1967 | Kessler et al. |
| 3,589,999 A | 6/1971 | McRae et al. |
| 3,590,035 A | 6/1971 | Damico et al. |
| 3,753,196 A | 8/1973 | Kurtz et al. |
| 3,761,418 A | 9/1973 | Parran et al. |
| 3,773,770 A | 11/1973 | Damico et al. |
| 3,852,441 A | 12/1974 | Kooistra et al. |
| 3,929,678 A | 12/1975 | Laughlin et al. |
| 3,940,482 A | 2/1976 | Grand et al. |
| 3,958,581 A | 5/1976 | Abegg et al. |
| 3,959,461 A | 5/1976 | Bailey et al. |
| 3,964,500 A | 6/1976 | Drakoff et al. |
| 4,055,655 A | 10/1977 | Maurer et al. |
| 4,089,945 A | 5/1978 | Brinkman et al. |
| 4,152,416 A | 5/1979 | Spitzer et al. |
| 4,161,526 A | 7/1979 | Gorman et al. |
| 4,197,865 A | 4/1980 | Jacquet et al. |
| 4,217,914 A | 8/1980 | Jacquet et al. |
| 4,323,683 A | 4/1982 | Bolich et al. |
| 4,345,080 A | 8/1982 | Bolich et al. |
| 4,364,387 A | 12/1982 | Larkin et al. |
| 4,379,753 A | 4/1983 | Bolich et al. |
| 4,381,919 A | 5/1983 | Jacquet et al. |
| 4,387,090 A | 6/1983 | Bolich et al. |
| 4,422,853 A | 12/1983 | Jacquet et al. |
| 4,470,982 A | 9/1984 | Winkler et al. |
| 4,507,280 A | 3/1985 | Pohl et al. |
| 4,529,586 A | 7/1985 | DeMarco et al. |
| 4,565,647 A | 1/1986 | Llenado et al. |
| 4,608,183 A | 8/1986 | Rossmoore et al. |
| 4,663,158 A | 5/1987 | Wolfram et al. |
| 4,666,616 A | 5/1987 | Rossmoore et al. |
| 4,670,430 A | 6/1987 | Imamura et al. |
| 4,686,254 A | 8/1987 | Lochhead et al. |
| 4,704,272 A | 11/1987 | Oh et al. |
| 4,708,863 A | 11/1987 | Bews et al. |
| 4,788,006 A | 11/1988 | Bolich et al. |
| 4,834,767 A | 5/1989 | Helioff et al. |
| 4,885,107 A | 12/1989 | Wetzel et al. |
| 4,898,585 A | 2/1990 | Borsanyi et al. |
| 5,034,218 A | 7/1991 | Duvel et al. |
| 5,057,153 A | 10/1991 | Ruggiero et al. |
| 5,104,646 A | 4/1992 | Bolich et al. |

(Continued)

FOREIGN PATENT DOCUMENTS

| | | |
|---|---|---|
| CN | 1658830 A | 8/2005 |
| DE | 10005162 A1 | 8/2001 |

(Continued)

OTHER PUBLICATIONS

Barry & Rowe, *The Characterization by Small Angle X-Ray Scattering of a Gel with a Lamellar Structure*, International Journal of Pharmaceuticals, 1989.

(Continued)

*Primary Examiner* — Necholus Ogden, Jr.
(74) *Attorney, Agent, or Firm* — James T. Fondriest

(57) ABSTRACT

A shampoo composition having from about 5% to about 50% of a combination of sodium lauryl sulfate and sodium laureth-n sulfate, less than 3.82% of sodium laureth-n sulfate having n>1. The shampoo composition further includes from about 0.5% to about 3% of a co-surfactant selected from the group consisting of amphoteric, zwitterionic, and nonionic surfactants. The shampoo composition has a dispersed gel network phase having at least 0.05% of one or more fatty alcohols, at least 0.01% of one or more secondary surfactants, and water. The shampoo composition further includes at least about 20% of an aqueous carrier. The shampoo composition further has an enthalpy of transition from about 0 J/g to about 0.2 J/g as measured according to differential scanning calorimetry in a peak melt transition temperature range between about 18° C. to about 30° C.

20 Claims, No Drawings

(56) References Cited

U.S. PATENT DOCUMENTS

| | | | |
|---|---|---|---|
| 5,106,609 | A | 4/1992 | Bolich et al. |
| 5,106,613 | A | 4/1992 | Hartnett et al. |
| 5,114,898 | A | 5/1992 | Pinnavaia et al. |
| 5,154,847 | A | 10/1992 | LaPetina et al. |
| 5,186,928 | A | 2/1993 | Birtwistle et al. |
| 5,202,048 | A | 4/1993 | Bartolo et al. |
| 5,227,156 | A | 7/1993 | Weise et al. |
| 5,248,445 | A | 9/1993 | Rizvi et al. |
| RE34,584 | E | 4/1994 | Grote et al. |
| 5,358,667 | A | 10/1994 | Bergmann et al. |
| 5,462,589 | A | 10/1995 | Nicholas et al. |
| 5,466,425 | A | 11/1995 | Adams et al. |
| 5,478,501 | A | 12/1995 | Rau |
| 5,518,774 | A | 5/1996 | Kappock et al. |
| 5,540,954 | A | 7/1996 | Nicholas et al. |
| 5,562,995 | A | 10/1996 | Kappock et al. |
| 5,614,538 | A | 3/1997 | Nelson et al. |
| 5,674,478 | A | 10/1997 | Dodd et al. |
| 5,696,169 | A | 12/1997 | Arima et al. |
| 5,710,114 | A | 1/1998 | Pyles et al. |
| 5,726,137 | A | 3/1998 | Patel et al. |
| 5,750,122 | A | 5/1998 | Evans et al. |
| 5,756,076 | A | 5/1998 | Cervantes et al. |
| 5,785,962 | A | 7/1998 | Hinz et al. |
| 5,798,121 | A | 8/1998 | Cauwet et al. |
| 5,837,661 | A | 11/1998 | Evans et al. |
| 5,853,707 | A | 12/1998 | Wells |
| 5,854,319 | A | 12/1998 | O'Lenick et al. |
| 5,874,476 | A | 2/1999 | Hsu et al. |
| 5,876,705 | A | 3/1999 | Uchiyama et al. |
| 5,880,076 | A | 3/1999 | Vermeer et al. |
| 5,883,154 | A | 3/1999 | Kappock et al. |
| 5,939,059 | A | 8/1999 | Franklin et al. |
| 5,939,203 | A | 8/1999 | Kappock et al. |
| 5,955,066 | A | 9/1999 | Sako et al. |
| 5,965,515 | A | 10/1999 | Rau |
| 5,997,851 | A | 12/1999 | Cox et al. |
| 6,017,562 | A | 1/2000 | Kaufman et al. |
| 6,034,043 | A | 3/2000 | Fujiwara et al. |
| 6,303,109 | B1 | 10/2001 | Foerster et al. |
| 6,309,628 | B1 | 10/2001 | Ansmann et al. |
| 6,333,040 | B1 | 12/2001 | Boyxen et al. |
| RE37,793 | E | 7/2002 | Domenico et al. |
| 6,495,538 | B2 | 12/2002 | Fliss et al. |
| 6,521,238 | B1 | 2/2003 | Muller et al. |
| RE38,130 | E | 6/2003 | Adams |
| 6,719,967 | B1 | 4/2004 | Brown |
| 6,774,096 | B1 | 8/2004 | Paye et al. |
| 6,908,912 | B2 | 6/2005 | Rioux et al. |
| 7,303,744 | B2 * | 12/2007 | Wells et al. ............... 424/70.28 |
| 2001/0047039 | A1 | 11/2001 | McManus et al. |
| 2002/0012646 | A1 | 1/2002 | Royce et al. |
| 2002/0119113 | A1 | 8/2002 | Ellis et al. |
| 2002/0169283 | A1 | 11/2002 | Lu et al. |
| 2003/0095938 | A1 | 5/2003 | Casero et al. |
| 2003/0119805 | A1 | 6/2003 | Fliss et al. |
| 2003/0130145 | A1 | 7/2003 | Patel et al. |
| 2003/0171231 | A1 | 9/2003 | Shana'a et al. |
| 2003/0185779 | A1 | 10/2003 | Mitsumatsu et al. |
| 2003/0215522 | A1 | 11/2003 | Johnson et al. |
| 2003/0223952 | A1 | 12/2003 | Wells et al. |
| 2003/0224955 | A1 | 12/2003 | Ribery et al. |
| 2004/0058855 | A1 | 3/2004 | Schwartz et al. |
| 2004/0167114 | A1 | 8/2004 | Fliss et al. |
| 2004/0191331 | A1 | 9/2004 | Schwartz et al. |
| 2004/0197294 | A1 | 10/2004 | Seipel et al. |
| 2004/0223941 | A1 | 11/2004 | Schwartz et al. |
| 2004/0234471 | A1 | 11/2004 | Corbella |
| 2004/0266886 | A1 | 12/2004 | Seipel et al. |
| 2005/0031569 | A1 | 2/2005 | Seipel et al. |
| 2005/0143268 | A1 | 6/2005 | Midha |
| 2005/0181067 | A1 | 8/2005 | Yokoyama et al. |
| 2005/0202984 | A1 | 9/2005 | Schwartz et al. |
| 2006/0024256 | A1 | 2/2006 | Wells |
| 2006/0024381 | A1 | 2/2006 | Schwartz et al. |
| 2006/0045861 | A1 | 3/2006 | Bejger et al. |
| 2006/0251605 | A1 | 11/2006 | Belamr |
| 2006/0269501 | A1 | 11/2006 | Johnson et al. |
| 2006/0269502 | A1 | 11/2006 | Johnson et al. |
| 2007/0110696 | A1 | 5/2007 | Johnson et al. |
| 2007/0110700 | A1 | 5/2007 | Wells |
| 2007/0128147 | A1 | 6/2007 | Schwartz et al. |
| 2008/0152611 | A1 | 6/2008 | Wells et al. |
| 2008/0187507 | A1 | 8/2008 | Johnson et al. |

FOREIGN PATENT DOCUMENTS

| | | |
|---|---|---|
| EP | 0037318 A1 | 10/1981 |
| EP | 0077630 | 4/1985 |
| EP | 0555690 | 8/1993 |
| EP | 0627216 A2 | 12/1994 |
| EP | 0976393 A1 | 2/2000 |
| EP | 1123693 | 2/2000 |
| EP | 1082086 | 3/2001 |
| EP | 1161869 | 12/2001 |
| FR | 2478467 | 9/1981 |
| FR | 2593801 | 8/1987 |
| GB | 849433 | 9/1960 |
| GB | 2177108 | 1/1987 |
| JP | 52/092881 | 8/1977 |
| JP | 6134227 | 5/1994 |
| JP | 7118103 | 5/1995 |
| JP | 2000/103724 | 4/2000 |
| JP | 2001/181145 | 7/2001 |
| JP | 2001/311099 | 11/2001 |
| JP | 2002/104940 | 4/2002 |
| JP | 2004/262805 | 9/2004 |
| JP | 2004/292387 | 10/2004 |
| JP | 2004/292390 | 10/2004 |
| JP | 2004/307463 | 11/2004 |
| JP | 2005/022983 | 1/2005 |
| JP | 2005/187342 A | 7/2005 |
| JP | 2006/063044 | 3/2006 |
| WO | WO 9308787 | 5/1993 |
| WO | WO 9410973 | 5/1994 |
| WO | WO 9501152 | 1/1995 |
| WO | WO 9625913 | 8/1996 |
| WO | WO 9714396 | 4/1997 |
| WO | WO 9847372 | 10/1998 |
| WO | WO 9938475 | 8/1999 |
| WO | WO 9951199 | 10/1999 |
| WO | WO 9959540 | 11/1999 |
| WO | WO 0066081 | 11/2000 |
| WO | WO 0100149 | 1/2001 |
| WO | WO 0117492 | 3/2001 |
| WO | WO 0139735 | 6/2001 |
| WO | WO 0178657 | 10/2001 |
| WO | WO 03032934 | 10/2001 |
| WO | WO 0219977 | 3/2002 |
| WO | WO 0222091 | 3/2002 |
| WO | WO 0232361 | 4/2002 |
| WO | WO 02076422 | 10/2002 |
| WO | WO 02080943 | 10/2002 |
| WO | WO 03101418 | 12/2003 |
| WO | WO 2005/048959 | 6/2005 |

OTHER PUBLICATIONS

Barry & Saunders, *Kinetics of Structure Build-up in Self Bodied Emulsions Stabalized by Mixed Emulsifiers*, Journal of Colloid Science, vol. 41, 1972.

Barry, B.W., Structure and Rheology of Emulsions Stabalized by Mixed Emulsifiers, British Society of Rheology, 1970.

Benton et al, Phase Behavior and Network Formation in a Cationic Surfactant-Fatty Alcohol System, JAOCS, vol. 64, 1987.

Burgess, J.D., Practical Analysis of Complex Coacervate Systems, Journal of Colloid Science, vol. 140, 1990.

CTFA Cosmetic Ingredient Dictionary, 1982, 3rd Edition, The Cosmetic, Toiletry & Fragrance Association, Inc., Washington, DC (*book not included*).

Eccleston, G.M., *Application of Emulsion Stability Theories to Mobile and Semisolid o/w Emulsions*, Cosmetics Magazine, vol. 101, 1986.

(56) References Cited

OTHER PUBLICATIONS

Eccleston, G.M., *Application of Emulsion Theory to Complex and Real Systems*, International Journal of Cosmetic Science, 1985.

Eccleston, G.M., *Formulating Cosmetic Emulsions*, Cosmetics Magazine, vol. 112, 1997.

Eccleston, G.M., *Functions of Mixed Emulsifiers and Emulsifying Waxes in Dermatological Lotions and Creams*, Colloids and Surfaces, vol. 123, 1997.

Eccleston, G.M., *Microstructural Changes During Storage of Cetostearyl Alcohol/Polyoxyethylene Alkyl Ether Surfactants*, University of Strathclyde, 1988.

Eccleston, G.M., *Multiple Phase Oil and Water Emulsions*, Journal of Cosmetic Chemists, 1990.

Eccleston, G.M., *Structure and Rheology of Semisolid o/w Creams Containing Cetyl Alcohol/Non-ionic Surfactant Mixed Emulsifier and Different Polymers*, International Journal of Cosmetic Science, 2004.

Eccleston, G.M., Synchrotron X-ray Investigations into the Lamellar Gel Phase Formed in Creams Prepared with Fatty Alcohols, International Journal of Pharmaceuticals, 2000.

Eccleston, G.M., The Influence of Fatty Alcohols on the Structure and Stability of Creams Preapred with Fatty Alcohols, International Journal of Cosmetic Science, 1982.

Encyclopedia of Polymer Science and Engineering, John Wiley & Sons, vol. 15, 1989 (*book not included*).

Griffin, W.C., Calculation of HLB Values of Non-Ionic Surfactants, Journal of the Society of Cosmetic Chemists; 1954. vol. 5, pp. 249-235.

Korhonen et al, Rheological Properties of Three Component Creams Containing Sorbitan Monoesters as Surfactants, International Journal of Pharmaceuticals, 2002.

Louden et al, A Preliminary Examination of the Structure of Gels and Emulsions Containing Cetostearyl Alcohol, International Journal of Pharmaceuticals, 1985.

McCutcheon, Emulsifiers and Detergents, MC Pub Company, 1989 (*book not included*).

Noll, W., Chemistry and Technology of Silicones, Academic Press, 1968 (book not included).

Patel et al, Properties of Cetrimide / Cetostearyl Alcohol Ternary Gels; Preparation Effects, International Journal of Pharmaceuticals, 1985.

Savic et al, *Colloidal Microstructure of Binary Systems and Model Creams Stablized with an Alkylpolyglucoside Emulsifier*, Colloid Polymer Science, vol. 283, 2004.

Saxton, C., *Antiplaque Effects and Mode of Action of a Combination of Zinc Citrate and a Nonionic Antimicrobial Agent*, Scandinavian Journal, vol. 96, 1988.

Suzuki et al, *Secondary Droplet Emulsion: Mechanism & Effects of Liquid Crystal Formation in o/w Emulsion*, Journal of Dispersion Science, 1984.

Van Cutsem, Journal of the American Academy of Dermatology, XP-002288119, 1998.

Van Oss, C.J., Coacervation, Complex Coacervation and Flocculation, Journal of Dispersion Science, vol. 9, 1989.

Yoon et al, *A Study of Gel Structure in the Nonionic Surfactant / Cetostearyl Alcohol / Water Ternary Systems by Differential Scanning Calorimeter*, Journal of Dispersion Science, 1999.

\* cited by examiner

SHAMPOO COMPOSITION CONTAINING A GEL NETWORK

FIELD OF THE INVENTION

The present invention relates to a shampoo composition containing a dispersed gel network phase and containing less than about 3.82% of sodium laureth-n sulfate by weight of said shampoo composition wherein N>1. More particularly, the present invention relates to such a shampoo composition containing greater than 0.5% sodium laureth-1 sulfate, and having an enthalpy of transition from about 0 J/g to about 0.2 J/g as measured according to differential scanning calorimetry in a peak melt transition temperature range between about 18° C. to about 30° C.

BACKGROUND OF THE INVENTION

Human hair becomes soiled due to its contact with the surrounding environment and from the sebum secreted by the scalp. The soiling of hair causes it to have a dirty feel and an unattractive appearance. The soiling of the hair necessitates shampooing with frequent regularity.

Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hair's natural oils.

A variety of approaches have been developed to alleviate these after-shampoo problems. One approach is the application of hair shampoos which attempt to both cleanse and condition the hair from a single product.

In order to provide hair conditioning benefits in a cleansing shampoo base, a wide variety of conditioning actives have been proposed. Traditionally, shampoos have used cationic polymers to form coacervate for conditioning benefits. However, these shampoo compositions generally do not deliver satisfactory smooth feel in dry hair. The use of shampoo compositions comprising a dispersed fatty alcohol gel network phase has been proposed to achieve improved wet feel and dry conditioning benefit while not interfering with cleansing efficacy. However, stability issues can arise when surfactant crystallizes out of solution at or near room temperature.

Based on the foregoing, there is a need for a shampoo which can provide improved conditioning benefit for dry hair, while not interfering with the cleansing efficacy, nor providing negative feel to the hair when dried. Specifically, there is a need to provide long lasting moisturized feel, smooth feel, and manageability control to the hair when in dry hair, yet not leave the hair feeling greasy, as well as to provide softness and ease of combing when the hair is wet.

SUMMARY OF THE INVENTION

The present invention is directed to a shampoo composition comprising: (a) from about 5% to about 50% of a combination of sodium lauryl sulfate and sodium laureth-n sulfate by weight of the shampoo composition, and less than 3.82% of sodium laureth-n sulfate by weight of said shampoo composition wherein n>1; (b) from about 0.5% to about 3% of a co-surfactant selected from the group consisting of amphoteric, zwitterionic, and nonionic surfactants, by weight of said shampoo composition; (c) a dispersed gel network phase comprising: (i) at least about 0.05% of one or more fatty alcohols, by weight of the shampoo composition; (ii) at least about 0.01% of one or more secondary surfactants, by weight of the shampoo composition; and (iii) water; and (d) at least about 20% of an aqueous carrier, by weight of the shampoo composition; wherein said shampoo composition has an enthalpy of transition from about 0 J/g to about 0.2 J/g as measured according to differential scanning calorimetry in a peak melt transition temperature range between about 18° C. to about 30° C.

The present invention also is directed to a process of making the shampoo composition described above.

These and other features, aspects, and advantages of the present invention will become evident to those skilled in the art from a reading of the present disclosure.

DETAILED DESCRIPTION OF THE INVENTION

While the specification concludes with claims which particularly point out and distinctly claim the invention, it is believed the present invention will be better understood from the following description.

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

The term "charge density," as used herein, refers to the ratio of the number of positive charges on a polymer to the molecular weight of said polymer.

The term "comprising," as used herein, means that other steps and other ingredients which do not affect the end result can be added. This term encompasses the terms "consisting of" and "consisting essentially of." The compositions and methods/processes of the present invention can comprise, consist of, and consist essentially of the elements and limitations of the invention described herein, as well as any of the additional or optional ingredients, components, steps, or limitations described herein.

The term "polymer," as used herein, includes materials whether made by polymerization of one type of monomer or made by two (i.e., copolymers) or more types of monomers.

The term "suitable for application to human hair," as used herein, means that the compositions or components thereof so described are acceptable for use in contact with human hair and the scalp and skin without undue toxicity, incompatibility, instability, allergic response, and the like.

The term "water soluble," as used herein, means that the material is soluble in water in the present composition. In general, the material should be soluble at 25° C. at a concentration of 0.1% by weight of the water solvent, alternatively at 1%, alternatively at 5%, and alternatively at 15%.

Shampoo Composition

As used herein, the term "gel network" refers to a lamellar or vesicular solid crystalline phase which comprises at least one fatty alcohol, at least one secondary surfactant, and water or other suitable solvents. In embodiments of the present invention this gel network is further combined with a detersive surfactant, such as an anionic surfactant, to form a shampoo product. In one embodiment of the present invention the anionic surfactant is sodium lauryl sulfate (SLS). The use of SLS in combination with a gel network in a shampoo can lead to difficulties with formulation. The SLS and sodium laureth-1 sulfate (SLE1S) in the system have a higher packing coefficient. This can result in making the shampoo products more elastic, and thus less consumer desirable, and can also result in both reducing the solubility of the SLS, and in forming SLS crystals.

Embodiments of the present invention balance the solubility of SLS while having a shampoo of acceptable rheology or elasticity. The elasticity is important in order to have good dispensing from the bottle, good spread of product through the hands and hair. Additionally, products that spread well through the hair are faster to lather and more acceptable to the consumer. Embodiments of shampoo compositions of the present invention comprise: (a) from about 9% to about 17% of one or more anionic surfactants by weight of the shampoo composition and less than about 3.82% of sodium laureth-n sulfate by weight of said shampoo composition wherein n>1; (b) from about 0.5% to about 3% of a co-surfactant selected from the group consisting of amphoteric, zwitterionic, and nonionic surfactants, by weight of said shampoo composition; (c) a dispersed gel network phase comprising: (i) at least about 0.05% of one or more fatty alcohols, by weight of the shampoo composition; (ii) at least about 0.01% of one or more secondary surfactants, by weight of the shampoo composition; and (iii) water; and (d) at least about 20% of an aqueous carrier, by weight of the shampoo composition; wherein said shampoo composition has an enthalpy of transition from about 0 J/g to about 0.2 J/g as measured according to differential scanning calorimetry in a peak melt transition temperature range between about 18° C. to about 30° C. Each of these components, as well as optional components, is described in detail hereinafter. In one embodiment of the present invention n>1, 2, 3, 4, 5, 6, 7 and less than 7, 6, 5, 4, 3, 2 and any combination thereof.

Detersive Surfactant

The shampoo composition of the present invention comprises one or more detersive surfactants. The detersive surfactant component is included in shampoo compositions of the present invention to provide cleansing performance. The detersive surfactant may be selected from anionic detersive surfactant, zwitterionic, or amphoteric detersive surfactant, or a combination thereof. Such surfactants should be physically and chemically compatible with the components described herein, or should not otherwise unduly impair product stability, aesthetics or performance.

Suitable anionic detersive surfactant components for use in the composition herein include those which are known for use in hair care or other personal care shampoo compositions. In one embodiment, the anionic detersive surfactant may be a combination of sodium lauryl sulfate and sodium laureth-n sulfate. The concentration of the anionic surfactant component in the composition should be sufficient to provide the desired cleaning and lather performance, and generally range from about 5% to about 50%, alternatively from about 8% to about 30%, alternatively from about 9% to about 25%, and alternatively from about 10% to about 17%, by weight of the composition.

Suitable zwitterionic or amphoteric detersive surfactants for use in the composition herein include those which are known for use in hair care or other personal shampoo compositions. Concentration of such amphoteric detersive surfactants range from about 0.5% to about 20%, alternatively from about 1% to about 10%. Non-limiting examples of suitable zwitterionic or amphoteric surfactants are described in U.S. Pat. Nos. 5,104,646 and 5,106,609.

Additional anionic surfactants suitable for use herein include alkyl and alkyl ether sulfates of the formula $ROSO_3M$ and $RO(C_2H_4O)_xSO_3M$, wherein R is alkyl or alkenyl of from about 8 to about 18 carbon atoms, x is 1 to 10, and M is a water-soluble cation such as ammonium, sodium, potassium, and triethanolamine cation or salts of the divalent magnesium ion with two anionic surfactant anions. The alkyl ether sulfates may be made as condensation products of ethylene oxide and monohydric alcohols having from about 8 to about 24 carbon atoms. The alcohols can be derived from fats such as coconut oil, palm oil, palm kernel oil, or tallow, or can be synthetic.

Other suitable anionic surfactants include water-soluble salts of the organic, sulfonic acids of the general formula $[R^1-SO_3M]$. $R^1$ being a straight chaing aliphatic hydrocarbon radical having from 13 to 17 carbon atoms, alternatively from 13 to 15 carbon atoms. M is a water soluble cation such as ammonium, sodium, potassium, and triethanolamine cation or salts of the divalent magnesium ion with two anionic surfactant anions. These materials are produced by the reaction of $SO_2$ and $O_2$ with suitable chain length normal paraffins ($C_{14}$-$C_{17}$) and are sold commercially as sodium paraffin sulfonates.

Examples of additional anionic surfactants suitable for use herein include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium trideceth sulfate, sodium tridecyl sulfate, sodium methyl lauroyl taurate, sodium methyl cocoyl taurate, sodium lauroyl isethionate, sodium cocoyl isethionate, sodium laurethsulfosuccinate, sodium laurylsulfosuccinate, sodium tridecyl benzene sulfonate, sodium dodecyl benzene sulfonate, and mixtures thereof.

| Surfactant | Supplier | Activity | SLS | SLE1S | SLE2S | SLE3S | SLE > 3S |
|---|---|---|---|---|---|---|---|
| Sodium Lauryl Sulfate | Stepan STEOL SLS | 29% by weight | 100 | 0 | 0 | 0 | 0 |
| Sodium Laureth-1 Sulfate | Stepan STEOL SLES-1 | 26% by weight | 45.5 | 26.3 | 11.8 | 0.07 | 16.33 |
| Sodium Laureth-3 Sulfate | Stepan STEOL SLES-3 | 28% by weight | 18 | 16.7 | 12.6 | 12.4 | 40.30 |

Table of Surfactant Distributions

The shampoo composition of the present invention may further comprise additional surfactants for use in combination with the anionic detersive surfactant component described herein. Suitable additional surfactants include cationic and nonionic surfactants.

Non-limiting examples of other anionic, zwitterionic, amphoteric, cationic, nonionic, or optional additional surfactants suitable for use in the compositions are described in McCutcheon's, Emulsifiers and Detergents, 1989 Annual, published by M. C. Publishing Co., and U.S. Pat. Nos. 3,929,678; 2,658,072; 2,438,091; and 2,528,378.

Co-Surfactant

Co-surfactants are materials which are combined with the undecyl sulfate surfactant and optionally anionic surfactants to enhance lather volume and/or to modify lather texture. Typically these materials can be selected from a variety of families of structures including, but not limited to, amphoteric, zwitterionic, cationic, and nonionic. They are typically used with anionic surfactants in a weight ratio of 1:20 to 1:4, and alternatively in the 1:12 to 1:7 weight ratio.

The shampoo composition of the present invention may comprise from about 0.5 wt % to about 10 wt %, alternatively from about 0.5 wt % to about 5 wt %, alternatively from about 0.5 wt % to about 3 wt %, alternatively from about 0.5 wt % to about 2 wt %, and alternatively from about 0.5 wt % to about 1.75 wt % by weight of the composition of at least one suitable co-surfactant. The co-surfactant may serve to produce faster lather, facilitate easier rinsing, and/or mitigate harshness on the keratinous tissue. The co-surfactant further may aid in producing lather having more desirable texture, volume and/or other properties.

Amphoteric surfactants suitable for use herein include, but are not limited to derivatives of aliphatic secondary and tertiary amines in which the aliphatic radical can be straight or branched chain and wherein one substituent of the aliphatic substituents contains from about 8 to about 18 carbon atoms and one contains an anionic water solubilizing group, e.g., carboxy, sulfonate, sulfate, phosphate, or phosphonate. Examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378, and mixtures thereof. In one embodiment the amphoteric surfactants may selected from the family of betaines such as lauryolamphoacetate.

Zwitterionic surfactants suitable for use herein include, but are not limited to derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Other zwitterionic surfactants suitable for use herein include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, lauryl bis-(2-hydroxypropyl)alpha-carboxyethyl betaine, and mixtures thereof. The sulfobetaines may include coco dimethyl sulfopropyl betaine, stearyl dimethyl sulfopropyl betaine, lauryl dimethyl sulfoethyl betaine, lauryl bis-(2-hydroxyethyl)sulfopropyl betaine and mixtures thereof. Other suitable amphoteric surfactants include amidobetaines and amidosulfobetaines, wherein the $RCONH(CH_2)_3$ radical, wherein R is a $C_{11}$-$C_{17}$ alkyl, is attached to the nitrogen atom of the betaine.

Nonionic co-surfactants typically used in the present composition for enhancing lather volume or texture include water soluble materials like lauryl dimethylamine oxide, cocodimethylamine oxide, cocoamidopropylamine oxide, laurylamidopropyl amine oxide, etc. or alkylpolyethoxylates like laureth-4 to laureth-7 and water insoluble components such as cocomonoethanol amide, cocodiethanol amide, lauroylmonoethanol amide, alkanoyl isopropanol amides, and fatty alcohols like cetyl alcohol and oleyl achohol, and 2-hydroxyalkyl methyl ethers, etc.

Further suitable materials as co-surfactants herein include 1,2-alkylepoxides, 1,2-alkanediols, branched or straight chain alkyl glyceryl ethers (e.g., as disclosed in EP 1696023A1), 1,2-alkylcyclic carbonates, and 1,2-alkyl cyclicsulfites, particularly those wherein the alkyl group contains 6 to 14 carbon atoms in linear or branched configuration. Other examples include the alkyl ether alcohols derived from reacting $C_{10}$ or $C_{12}$ alpha olefins with ethylene glycol (e.g., hydroxyethyl-2-decyl ether, hydroxyethyl-2-dodecyl ether), as can be made according to U.S. Pat. Nos. 5,741,948; 5,994,595; 6,346,509; and 6,417,408.

Other nonionic surfactants may be selected from the group consisting of glucose amides, alkyl polyglucosides, sucrose cocoate, sucrose laurate, alkanolamides, ethoxylated alcohols and mixtures thereof. In one embodiment the nonionic surfactant is selected from the group consisting of glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

In a particular embodiment, the co-surfactant is selected from the group consisting of Cocomonoethanol Amide, Cocoamidopropyl Betaine, Laurylamidopropyl Betaine, Cocobetaine, lauryl betaine, lauryl amine oxide, sodium lauryl amphoacetate; alkyl glyceryl ethers, alkyl-di-glyceryl ethers, 1,2-alkyl cyclic sulfites, 1,2-alkyl cyclic carbonates, 1,2-alkyl-epoxides, alkyl glycidylethers, and alkyl-1,3-dioxolanes, wherein the alkyl group contains 6 to 14 carbon atoms in linear or branched configuration; 1,2-alkane diols where the total carbon content is from 6 to 14 carbon atoms linear or branched, methyl-2-hydroxy-decyl ethers, hydroxyethyl-2-dodecyl ether, hydroxyethyl-2-decyl ether, and mixtures thereof.

Cationic surfactants may be derived from amines that are protonated at the pH of the formulation, e.g. bis-hydroxyethyl lauryl amine, lauryl dimethylamine, lauroyl dimethyl amidoproplyl amine, cocoylamidopropyl amine, and the like. The cationic surfactants may also be derived from fatty quaternary ammonium salts such as lauryl trimethylammonium chloride and lauroylamidopropyl trimethyl ammonium chloride.

In one embodiment, the shampoo composition may comprise two or more phases to make a multiphase person care composition. One phase may comprise traditional personal care components, such as structured surfactants, and the second phase of multiphase personal care compositions of the present invention can comprise a benefit phase.

The benefit phase, when present, may be anhydrous and can be substantially free of water. The benefit phase can comprise less than about 5 wt % water, alternatively less than 3 wt % water, and alternatively less than 1 wt % water. The benefit phase can be substantially free of surfactant. The benefit phase can comprise less than about 5 wt % of surfactant, alternatively less than about 3 wt % of surfactant, and alternatively less than about 1 wt % surfactant.

The benefit phase may comprise hydrophobic moisturizing materials. The benefit phase can be comprised of the components selected from the group consisting of petrolatum, lanolin, hydrocarbon oils such as mineral oil, natural and synthetic waxes such as micro-crystalline waxes, paraffins, ozokerite, lanolin wax, lanolin alcohols, lanolin fatty acids, polyethylene, polybutene, polydecene and perhydrosqualene, volatile or non-volatile organosiloxanes and their derivatives such as dimethicones, cyclomethicones, alkyl siloxanes, polymethylsiloxanes and methylphenylpolysiloxanes, lanolin oil, esters such as isopropyl lanolate, acetylated lanolin, acetylated lanolin alcohols, lanolin alcohol linoleate, lanolin alcohol riconoleate natural and synthetic triglycerides such as castor oil, soy bean oil, sunflower seed oil, maleated soy bean oil, safflower oil, cotton seed oil, corn oil, walnut oil, peanut oil, olive oil, cod liver oil, almond oil, avocado oil, palm oil and sesame oil, castor oil derivatives, sefoses, and combinations thereof.

In one embodiment, the benefit phase may comprise a hydrophobic moisturizing material. Hydrophobic moisturizing materials suitable for use in particular multi-phase compositions may have a Vaughan Solubility Parameter ("VSP") of from about 5 $(cal/cm^3)^{1/2}$ to about 15 $(cal/cm^3)^{1/2}$, as defined by *Vaughan in Cosmetics and Toiletries*, Vol. 103. Non-limiting examples of hydrophobic moisturizing materials having VSP values ranging from about 5 to about 15 include the following: Cyclomethicone 5.92, Squalene 6.03, Petrolatum 7.33, Isopropyl Palmitate 7.78, Isopropyl Myristate 8.02, Castor Oil 8.90, Cholesterol 9.55, as reported in *Solubility, Effects in Product, Package, Penetration and Preservation*, C. D. Vaughan, Cosmetics and Toiletries, Vol. 103, October 1988.

The shampoo composition of the present invention, when in a multiphase form, may comprise structured surfactant that is suitable for application to keratinous tissue such as skin and/or hair. The part of the shampoo composition which contains the structured surfactant can comprise in one embodiment at least about 50% of anisotropic phase, and in a different embodiment from about 50% to about 90% of an anisotropic phase. Structured surfactants may comprise anionic, nonionic, cationic, zwitterionic, amphoteric surfactants, soap, and combinations thereof, as disclosed herein and in US 2007/0248562 A1, in combination with a suitable structurant.

Alkylamphoacetates are suitable structured surfactants used in the multiphase compositions herein for improved product mildness and lather. The most commonly used alkylamphoacetates are lauroamphoacetate and cocoamphoacetate. Alkylamphoacetates can be comprised of monoacetates and diacetates. In some types of alkylamphoacetates, diacetates are impurities or unintended reaction products. However, the presence of diacetate can cause a variety of unfavorable composition characteristics when present in amounts over 15% of the alkylamphoacetates.

Suitable nonionic surfactants for use herein are those selected from the group consisting of glucose amides, alkyl polyglucosides, sucrose cocoate, sucrose laurate, alkanolamides, ethoxylated alcohols and mixtures thereof. In one embodiment the nonionic surfactant is selected from the group consisting of glyceryl monohydroxystearate, isostearath-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

The structured surfactant may be in the form of a discrete structured domain, visibly distinct from the non-structured domain. Where the composition comprises both a structured and a non-structured phase, the structured domain can enable the incorporation of high levels of skin care actives that are not otherwise emulsified in the composition. In a particular embodiment the structured domain is an opaque structured domain. The opaque structured domain may be a lamellar phase, and may be a lamellar phase that produces a lamellar gel network.

In one embodiment, the structured surfactant is in the form of a lamellar phase, which provides resistance to shear, adequate yield to suspend particles and droplets, desirable rheology characteristics, and/or long term stability. The lamellar phase tends to have a viscosity that minimizes the need for viscosity modifiers.

Non-limiting examples of suitable structurants are described in U.S. Pat. No. 5,952,286, and include unsaturated and/or branched long chain ($C_8$-$C_{24}$) liquid fatty acids or ester derivative thereof; unsaturated and/or branched long chain liquid alcohol or ether derivatives thereof, and mixtures thereof. The structured surfactant also may comprise short chain saturated fatty acids such as capric acid and caprylic acid. Without being limited by theory, it is believed that the unsaturated part of the fatty acid of alcohol or the branched part of the fatty acid or alcohol acts to "disorder" the surfactant hydrophobic chains and induce formation of lamellar phase. Examples of suitable liquid fatty acids include oleic acid, isostearic acid, linoleic acid, linolenic acid, ricinoleic acid, elaidic acid, arichidonic acid, myristoleic acid, palmitoleic acid, and mixtures thereof. Examples of suitable ester derivatives include propylene glycol isostearate, propylene glycol oleate, glyceryl isostearate, glyceryl oleate, polyglyceryl diisostearate and mixtures thereof. Examples of alcohols include oleyl alcohol and isostearyl alcohol. Examples of ether derivatives include isosteareth or oleth carboxylic acid; or isosteareth or oleth alcohol. The structuring agent may be defined as having melting point below about 25° C.

The composition can comprise both an anisotropic and/or an isotropic phase. In a particular embodiment, the structured surfactant is in a visibly distinct phase of the composition.

If present, the composition may comprise a rheology modifier, wherein said rheology modifier comprises cellulosic rheology modifiers, cross-linked acrylates, cross-linked maleic anhydride co-methylvinylethers, hydrophobically modified associative polymers, or a mixture thereof.

An electrolyte, if used, can be added per se to the multiphase composition or it can be formed in situ via the counterions included in one of the raw materials. The electrolyte may include an anion comprising phosphate, chloride, sulfate or citrate and a cation comprising sodium, ammonium, potassium, magnesium or mixtures thereof. The electrolyte may be sodium chloride, ammonium chloride, sodium or ammonium sulfate. The electrolyte may be added to the structured surfactant phase of the multiphase composition in the amount of from about 0.1 wt % to about 15 wt % by weight, alternatively from about 1 wt % to about 6 wt % by weight, and alternatively from about 3 wt % to about 6 wt %, by weight of the structured surfactant composition.

In one embodiment of the present invention, the personal care composition comprises a structured surfactant phase comprising a mixture of at least one nonionic surfactant, and an electrolyte. In another embodiment, the surfactant phase can comprise a mixture of surfactants, water, at least one anionic surfactant, an electrolyte, and at least one alkanolamide.

Dispersed Gel Network Phase

The shampoo composition of the present invention comprises a dispersed gel network phase comprising one or more fatty alcohols. The dispersed gel network phase is included in shampoo compositions of the present invention to provide conditioning benefits. As used herein, the term "gel network" refers to a lamellar or vesicular solid crystalline phase which comprises at least one fatty alcohol as specified below, at least one secondary surfactant as specified below, and water or other suitable solvents. The lamellar or vesicular phase comprises bi-layers made up of a first layer comprising the fatty alcohol and the secondary surfactant and alternating with a second layer comprising the water or other suitable solvent. The term "solid crystalline", as used herein, refers to the structure of the lamellar or vesicular phase which forms at a temperature below the melt transition temperature of the layer in the gel network comprising the one or more fatty alcohols, the melt transition temperature being at least about 30° C. (i.e., slightly above about room temperature). The melt transition temperature may be measured by differential scanning calorimetry, a method of which is described below.

For purposes of clarification, the melt transition temperature of at least 30° C., which is referred to immediately above as part of the definition of "solid crystalline", is a different value from the melt transition temperature of the dispersed gel network phase of shampoo compositions of the present invention. In other words, a lamellar or vesicular phase as described above may be solid crystalline (i.e., at least 30° C.), but such a solid crystalline lamellar or vesicular phase is not necessarily a dispersed gel network phase of shampoo compositions of the present invention.

Gel networks which comprise, for example, fatty alcohols have been used for years in cosmetic creams and hair conditioners. Such cosmetic creams and hair conditioners, however, typically contain very low amounts, if any, of detersive surfactant. Thus, such known products do not provide a combination of cleansing and conditioning to the hair or skin.

Gel networks, generally, are further described by G. M. Eccleston, "Functions of Mixed Emulsifiers and Emulsifying Waxes in Dermatological Lotions and Creams", *Colloids and Surfaces A: Physiochem. and Eng. Aspects* 123-124 (1997) 169-182; and by G. M Eccleston, "The Microstructure of Semisolid Creams", *Pharmacy International*, Vol. 7, 63-70 (1986). In an embodiment of the present invention, the dispersed gel network phase is pre-formed. The term "pre-formed", as used herein, means that at least fifty percent of the mixture of the fatty alcohol, secondary surfactant, and water or other suitable solvent is substantially a solid crystalline phase when added to the other components of the shampoo composition.

According to this embodiment of the present invention, the gel network component of the present invention is prepared as a separate pre-mix, which, after being cooled, is subsequently incorporated with the detersive surfactant and the other components of the shampoo composition. Preparation of the gel network component is discussed in more detail below in the section entitled Process of Making a Shampoo Composition as well as in the Examples.

The cooled and pre-formed gel network component subsequently is added to the other components of the shampoo composition, including the detersive surfactant component. While not intending to be limited by theory, it is believed that incorporation of the cooled and pre-formed gel network component with the detersive surfactant and other components of the shampoo composition allows the formation of a substantially equilibrated lamellar dispersion ("ELD") in the final shampoo composition. The ELD is a dispersed lamellar or vesicular phase resulting from the pre-formed gel network component substantially equilibrating with the detersive surfactants, water, and other optional components, such as salts, which may be present in the shampoo composition. This equilibration occurs upon incorporation of the pre-formed gel network component with the other components of the shampoo composition and is effectively complete within about 24 hours after making. Shampoo compositions in which the ELD is formed provide hair with improved wet and dry conditioning benefits. Further, the ELD does not form if the components which comprise the gel network component (i.e., the fatty alcohol and the secondary surfactant combined with water) are added as individual components together with the other components of the shampoo composition in one mixing step, and not as a separate cooled pre-formed gel network component.

For purposes of clarification, as used herein, the term "ELD" refers to the same component of the shampoo compositions of the present invention as the phrase "dispersed gel network phase".

The presence of the gel network in the pre-mix and in the final shampoo composition in the form of the ELD can be confirmed by means known to one of skill in the art, such as X-ray analysis, optical microscopy, electron microscopy, and differential scanning calorimetry. A method of differential scanning calorimetry is described below. For methods of X-ray analysis, see U.S. 2006/0024256 A1.

In one embodiment of the present invention, the scale size of the dispersed gel network phase in the shampoo composition (i.e., the ELD) ranges from about 10 nm to about 500 nm. In another embodiment, the scale size of the dispersed gel network phase in the shampoo composition ranges from about 0.5 µm to about 10 µm. In yet another embodiment, the scale size of the dispersed gel network phase in the shampoo composition ranges from about 10 µm to about 150 µm.

The scale size distribution of the dispersed gel network phase in the shampoo composition may be measured with a laser light scattering technique, using a Horiba model LA 910 Laser Scattering Particle Size Distribution Analyzer (Horiba Instruments, Inc. Irvine Calif., USA). The scale size distribution in a shampoo composition of the present invention may be measured by combining 1.75 g of the shampoo composition with 30 mL of 3% $NH_4Cl$, 20 mL of 2% $Na_2HPO_4.7H_2O$, and 10 mL of 1% laureth-7 to form a mixture. This mixture is then stirred for 5 minutes. As appropriate for the individual Horiba instrument being used, samples in the range of 1 to 40 mL are taken and then injected into the Horiba instrument, which contains 75 mL of 3% $NH_4Cl$, 50 mL of 2% $Na_2HPO_4.7H_2O$, and 25 mL of 1% laureth-7, until the Horiba instrument reading is between 88-92% T, which is needed for the scale size measurement. Once this is achieved, a measurement is taken after 2 minutes of circulation through the Horiba instrument to provide the scale size measurement. A subsequent measurement is taken using a sample of the shampoo composition which has been heated above the melt transition temperature of all fatty materials present in the shampoo composition, such that the gel network component is melted. This subsequent measurement allows a scale size distribution to be taken of all of the remaining materials in the shampoo, which then can be compared to the scale size distribution of the first sample and assist in the analysis.

A. Fatty Alcohol

The gel network component of the present invention comprises at least one fatty alcohol. Individual fatty alcohol compounds or combinations of two or more different fatty alcohol compounds may be selected.

Fatty alcohols suitable for use in the present invention are those having from about 18 to about 70 carbon atoms, and in one embodiment from about 18 to about 60 carbon atoms, in another embodiment from about 18 to about 50 carbon atoms, in yet another embodiment from about 18 to about 40 carbon atoms, and in even yet another embodiment from about 18 to about 22 carbon atoms. These fatty alcohols may be straight or branched chain alcohols and may be saturated or unsaturated. Non-limiting examples of suitable fatty alcohols include stearyl alcohol, arachidyl alcohol, behenyl alcohol, C21 fatty alcohol (1-heneicosanol), C23 fatty alcohol (1-tricosanol), C24 fatty alcohol (lignoceryl alcohol, 1-tetracosanol), C26 fatty alcohol (1-hexacosanol), C28 fatty alcohol (1-octacosanol), C30 fatty alcohol (1-triacontanol), C20-40 alcohols (e.g., Performacol 350 and 425 Alcohols, available from New Phase Technologies), C30-50 alcohols (e.g., Performacol 550 Alcohol), C40-60 alcohols (e.g., Performacol 700 Alcohol), and mixtures thereof.

Mixtures of different fatty alcohols comprising one or more fatty alcohols having from about 18 to about 70 carbon atoms may also comprise some amount of one or more fatty alcohols or other fatty amphiphiles which have less than about 18 carbon atoms or greater than about 70 carbon atoms and still be considered to be within the scope of the present invention, provided that the resulting dispersed gel network phase has a melt transition temperature of at least about 38° C.

Such fatty alcohols suitable for use in the present invention may be of natural or vegetable origin, or they may be of synthetic origin.

The shampoo compositions of the present invention comprise fatty alcohol as part of the dispersed gel network phase in an amount of at least 0.05%, alternatively from about 0.05% to about 14%, alternatively from about 0.5% to about 10%, and alternatively from about 1% to about 8%, by weight of the shampoo composition.

In an embodiment of the present invention, the weight ratio of the fatty alcohol to the secondary surfactant in the gel network component is greater than about 1:9, alternatively from about 1:5 to about 100:1, and alternatively from about 1:1 to about 50:1.

B. Secondary Surfactant

The gel network component of the present invention also comprises a secondary surfactant. As used herein, "secondary surfactant" refers to one or more surfactants which are combined with the fatty alcohol and water to form the gel network of the present invention as a pre-mix separate from the other components of the shampoo composition. The secondary surfactant is separate from and in addition to the detersive surfactant component of the shampoo composition. However, the secondary surfactant may be the same or different type of surfactant or surfactants as that or those selected for the detersive surfactant component described above.

The shampoo compositions of the present invention comprise secondary surfactant as part of the pre-formed dispersed gel network phase in an amount from about 0.01% to about 15%, alternatively from about 0.1% to about 10%, and alternatively from about 0.2% to about 5%, by weight of the shampoo composition.

Suitable secondary surfactants include anionic, zwitterionic, amphoteric, cationic, and nonionic surfactants. The secondary surfactant may be selected from anionic, cationic, and nonionic surfactants, and mixtures thereof. For additional discussion of secondary surfactants which are suitable for use in the present invention, see U.S. 2006/0024256 A1.

Additionally, in an embodiment of the present invention, certain secondary surfactants which have a hydrophobic tail group with a chain length of from about 16 to about 22 carbon atoms. For such secondary surfactants, the hydrophobic tail group may be alkyl, alkenyl (containing up to 3 double bonds), alkyl aromatic, or branched alkyl. In such an embodiment, ithe secondary surfactant may be present in the gel network component relative to the fatty alcohol at a weight ratio from about 1:5 to about 5:1.

Mixtures of more than one surfactant of the above specified types may be used for the secondary surfactant of the present invention.

C. Water or Suitable Solvents

The gel network component of the present invention also comprises water or suitable solvents. The water or suitable solvent and the secondary surfactant together contribute to the swelling of the fatty alcohol. This, in turn, leads to the formation and the stability of the gel network. As used herein, the term "suitable solvent" refers to any solvent which can be used in the place of or in combination with water in the formation of the gel network of the present invention.

The shampoo compositions of the present invention comprise water or suitable solvents as part of the pre-formed dispersed gel network phase in an amount suitable to achieve a gel network when combined with fatty alcohol and secondary surfactant according to the present invention.

In one embodiment, the shampoo compositions of the present invention comprise as part of the pre-formed dispersed gel network phase at least about 0.05% of water or a suitable solvent, by weight of the shampoo composition.

In another embodiment of the present invention, the shampoo compositions comprise water or a suitable solvent as part of the pre-formed dispersed gel network phase is an amount relative to the amount of fatty alcohol at a weight ratio of at least about 1:1.

Enthalpy of Transition

According to the present invention, the shampoo composition has an enthalpy of transition from about 0 J/g to about 0.2 J/g as measured according to differential scanning calorimetry in a peak melt transition temperature range between about 18° C. to about 30° C. In one embodiment, the shampoo composition has an enthalpy of transition from about 0 J/g to about 0.1 J/g as measured according to differential scanning calorimetry in a peak melt transition temperature range between about 18° C. to about 30° C.

It is believed that, in the shampoo compositions of the present invention, having an enthalpy of transition from about 0 J/g to about 0.2 J/g as measured according to differential scanning calorimetry in a peak melt transition temperature range between about 18° C. to about 30° C. contributes to improved physical stability of the shampoo compositions while also delivering improved lather benefits.

The melt transition temperature may be obtained using differential scanning calorimetry according to the following method. Utilizing a TA Instruments Q100 DSC, approximately 50 mg of the gel network pre-mix or the final shampoo composition containing the gel network is placed into a stainless steel high volume DSC pan. The sample, along with an empty reference pan is placed into the instrument. The samples are analyzed using the following conditions/temperature program: Nitrogen Purge, Equilibrate @ 4.00° C. until an isothermal is reach for 2.00 min Ramp the temperature at a rate of 1.00° C./min to 75.00° C. Each sample is analyzed in duplicate. The resulting DSC data is analyzed using TA Instruments Universal Analysis Software.

The use of DSC to measure the melt transition temperature is further described by T. de Vringer et al., *Colloid and Polymer Science*, vol. 265, 448-457 (1987); and H. M. Ribeiro et al., *Intl. J. of Cosmetic Science*, vol. 26, 47-59 (2004).

Aqueous Carrier

The shampoo compositions of the present invention comprise an aqueous carrier. Typically, the compositions of the present invention are in the form of pourable liquids (under ambient conditions). The compositions, therefore, comprise an aqueous carrier at a level of at least about, alternatively from about 20% to about 95%, and alternatively from about 60% to about 85%, by weight of the compositions. The aqueous carrier may comprise water, or a miscible mixture of water and organic solvent. The aqueous carrier may also comprise water with minimal or no significant concentrations of organic solvent, except as otherwise incidentally incorporated into the composition as minor ingredients of other components.

Additional Components

The compositions of the present invention may further comprise one or more optional components known for use in hair care or personal care products, provided that the optional components are physically and chemically compatible with the components described herein, or do not otherwise unduly impair product stability, aesthetics or performance. Individual concentrations of such optional components may range from about 0.001% to about 10% by weight of the compositions.

Non-limiting examples of optional components for use in the composition include cationic polymers, conditioning agents (hydrocarbon oils, fatty esters, silicones), anti-dandruff agents, suspending agents, viscosity modifiers, dyes, nonvolatile solvents or diluents (water soluble and insoluble), pearlescent aids, foam boosters, additional surfactants or nonionic co-surfactants, pediculocides, pH adjusting agents, perfumes, preservatives, chelants, proteins, skin active agents, sunscreens, UV absorbers, and vitamins.

A. Deposition Aid

The shampoo compositions of the present invention may include a deposition aid. The deposition aid is included to effectively enhance deposition of the gel network component. The deposition aid can comprise any material that enhances the deposition of the gel network from the shampoo onto the hair and/or scalp.

The concentration of the deposition aid in the shampoo composition should be sufficient to effectively enhance the deposition of the gel network component and ranges from about 0.05% to about 5%, alternatively from about 0.075% to about 2.5%, and alternatively from about 0.1% to about 1.0%, by weight of the shampoo composition.

In one embodiment of the present invention, the deposition aid is a cationic polymer. Cationic polymers may have cationic charge densities of at least about 0.9 meq/g, alternatively at least about 1.2 meq/g, alternatively at least about 1.5 meq/g, alternatively less than about 7 meq/g, and alternatively less than about 5 meq/g, at the pH of intended use of the composition. The pH will generally range from about pH 3 to about pH 9, alternatively between about pH 4 and about pH 8. The "cationic charge density" of a polymer, as that term is used herein, refers to the ratio of the number of positive charges on the polymer to the molecular weight of the polymer. The average molecular weight of such suitable cationic polymers will generally be between about 10,000 and 10 million, alternatively between about 50,000 and about 5 million, and alternatively between about 100,000 and about 3 million.

Suitable cationic polymers for use in the composition include polysaccharide polymers, such as cationic cellulose derivatives and cationic starch derivatives, such as salts of hydroxyethyl cellulose reacted with trimethyl ammonium substituted epoxide. Other suitable cationic polymers include cationic guar gum derivatives, such as guar hydroxypropyltrimonium chloride. Further suitable cationic polymers include galactomannan polymer derivatives having a mannose to galactose ratio of greater than 2:1 on a monomer to monomer basis, such as cassia gum hydroxypropyltrimonium chloride.

B. Dispersed Particles

The composition of the present invention may include dispersed particles. Particles useful in the present invention can be inorganic, synthetic, or semi-synthetic in origin. If present in the compositions of the present invention, dispersed particles are incorporated in an amount from about 0.025% to about 20%, alternatively from about 0.05% to about 10%, alternatively from about 0.1% to about 5%, alternatively from about 0.25% to about 3%, and alternatively from about 0.5% to about 2%, by weight of the composition.

C. Nonionic Polymers

Polyalkylene glycols having a molecular weight of more than about 1000 are useful herein. Useful are those having the following general formula:

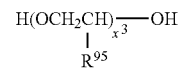

wherein $R^{95}$ is selected from the group consisting of H, methyl, and mixtures thereof. Polyethylene glycol polymers useful herein are PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

D. Additional Conditioning Agents

The compositions of the present invention may also comprise one or more conditioning agents which are in addition to the dispersed gel network phase. Conditioning agents include materials which are used to give a particular conditioning benefit to hair and/or skin. The conditioning agents useful in the compositions of the present invention typically comprise a water-insoluble, water-dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix.

In one embodiment, the shampoo composition of the present invention further comprises a non-volatile silicone oil. For an opaque composition embodiment, the shampoo composition comprises a non-volatile silicone oil having a particle size as measured in the shampoo composition from about 1 µm to about 50 µm. In an embodiment of the present invention for small particle application to the hair, the shampoo composition comprises a non-volatile silicone oil having a particle size as measured in the shampoo composition from about 100 nm to about 1 μm. For a substantially clear composition embodiment, the shampoo composition comprises a non-volatile silicone oil having a particle size as measured in the shampoo composition of less than about 100 nm.

When present, the one or more conditioning agents are in an amount from about 0.01% to about 10%, alternatively from about 0.1% to about 8%, and alternatively from about 0.2% to about 4%, by weight of the composition.

The conditioning agents may be present in the dispersed gel network phase or may be added to the final shampoo composition as a separate component such that they are present primarily in the continuous phase of the shampoo.

E. Anti-Dandruff Actives

The compositions of the present invention may also contain an anti-dandruff active. Suitable non-limiting examples of anti-dandruff actives include pyridinethione salts, azoles, selenium sulfide, particulate sulfur, keratolytic agents, and mixtures thereof. Such anti-dandruff actives should be physically and chemically compatible with the components of the composition, and should not otherwise unduly impair product stability, aesthetics or performance.

When present in the composition, the anti-dandruff active is included in an amount from about 0.01% to about 5%, alternatively from about 0.1% to about 3%, and alternatively from about 0.3% to about 2%, by weight of the composition.

F. Humectants

The compositions of the present invention may contain a humectant. The humectants herein are selected from the group consisting of polyhydric alcohols, water soluble alkoxylated nonionic polymers, and mixtures thereof. The humectants, when used herein, may be present in an amount by weight of the composition from about 0.1% to about 20%, alternatively from about 0.5% to about 5%.

G. Suspending Agent

The compositions of the present invention may further comprise a suspending agent at concentrations effective for suspending water-insoluble material in dispersed form in the compositions or for modifying the viscosity of the composition. Such concentrations range from about 0.1% to about 10%, alternatively from about 0.3% to about 5.0%, by weight of the composition.

Suspending agents useful herein include crystalline suspending agents which can be categorized as acyl derivatives, long chain amine oxides, and mixtures thereof. These suspending agents are described in U.S. Pat. No. 4,741,855. These suspending agents may include ethylene glycol esters of fatty acids having from about 16 to about 22 carbon atoms. Alternatives include ethylene glycol stearates, both mono and distearate, and the distearate containing less than about 7% of the mono stearate.

H. Other Optional Components

The compositions of the present invention may contain other optional components. Optional components may be present in the dispersed gel network phase or may be added to the final shampoo composition as separate components.

For example, the compositions of the present invention may contain water-soluble and water-insoluble vitamins such as vitamins B1, B2, B6, B12, C, pantothenic acid, pantothenyl ethyl ether, panthenol, biotin and their derivatives, and vitamins A, D, E, and their derivatives. The compositions of the present invention may also contain water-soluble and water-insoluble amino acids such as asparagine, alanine, indole, glutamic acid and their salts, and tyrosine, tryptamine, lysine, histadine and their salts. The compositions of present invention may further comprise materials useful for hair loss prevention and hair growth stimulants or agents.

Any other suitable optional component can also be included in the composition of the present invention, such as those ingredients that are conventionally used in given product types. The CTFA Cosmetic Ingredient Handbook, Tenth Edition (2004), published by the Cosmetic, Toiletry, and Fragrance Association, Inc., Washington, D.C., describes a wide variety of nonlimiting materials that can be added to the composition herein. Examples of these ingredient classes include, but are not limited to: abrasives, absorbents, aesthetic components such as perfumes and fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antibacterial agents, antifungal agents, antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, plant derivatives, plant extracts, plant tissue extracts, plant seed extracts, plant oils, botanicals, botanical extracts, preservatives, propellants, reducing agents, sebum control agents, sequestrants, skin bleaching and lightening agents, (e.g., hydroquinone, kojic acid, ascorbic acid, magnesium ascorbyl phosphate, ascorbyl glucoside, pyridoxine), enzymes, coenzymes, skin-conditioning agents (e.g., humectants and occlusive agents), skin soothing and/or healing agents and derivatives (e.g., panthenol, and derivatives such as ethyl panthenol, aloe vera, pantothenic acid and its derivatives, allantoin, bisabolol, and dipotassium glycyrrhizinate), skin treating agents (e.g., vitamin D compounds, mono-, di-, and tri-terpenoids, beta-ionol, cedrol), thickeners (including a mono- or divalent salt such as sodium chloride), and vitamins, their derivatives, and combinations thereof.

When certain oil-soluble components, such as perfumes and fragrances, amino acids, water-insoluble vitamins, and the like, are present in the dispersed gel network phase, either by incorporating such components directly into the gel network component pre-mix or separately into the shampoo composition and consequently some amount of such components migrate into the dispersed gel network phase during equilibration, they may be effectively deposited on hair and/or skin. To obtain very effective deposition of oil-soluble components on hair and/or skin via their presence in the dispersed gel network phase, oil-soluble component compositions which comprise no less than about 60% of ingredients having a Clog P of about 3 or higher may be used. For further discussion on Clog P and how to determine its value for a variety of materials, see, for example, U.S. Pat. Nos. 5,849, 310 and 5,500,154 as well as EP 1 533 364.

Viscosity

According to the present invention, the shampoo composition has a zero shear viscosity between about 1,000 cps to about 30,000 cps with a frequency at the crossover point greater than about 2 Hz. In one embodiment, the shampoo composition has a zero shear viscosity between about 5,000 cps and about 20,000 cps with a frequency at a crossover point greater than about 3 Hz.

It is believed that, in the shampoo compositions of the present invention, having a zero shear viscosity between about 1,000 cps and about 30,000 cps with a frequency at the crossover point greater than about 2 Hz allows the shampoo to be easily dispensed and spread through the hair. Spreading and dissolution will also increase the speed of lather generation.

The zero shear viscosity can be obtained using the AR2000 rheometer with a peak hold for 30 seconds at 0.01 s$^{-1}$. The frequency of crossover can be obtained by doing an oscillatory frequency sweep from 0.1 to 100 Hz. The crossover point is the point at which the G' and G" cross. The frequency at crossover is the frequency at which that occurs. A cross hatched parallel plate can be used to increase sample size to 1 ml and penetrate into the sample to prevent slipping. The material of the parallel plate is acrylic to allow lower geometry inertia to help with poor resolution at higher frequencies.

Process of Making a Shampoo Composition

An aspect of the invention relates to a process of making a shampoo composition of the present invention. The process of making a shampoo composition comprises (a) combining a fatty alcohol, a secondary surfactant, and water at a temperature sufficient to allow partitioning of the secondary surfactant and the water into the fatty alcohol to form a pre-mix; (b) cooling the pre-mix below the chain melt temperature of the fatty alcohol to form a gel network; (c) adding the gel network to one or more detersive surfactants and an aqueous carrier to form a shampoo composition which comprises a dispersed gel network phase having a melt transition temperature of at least about 38° C.

As discussed above, in one embodiment of the present invention, the gel network component is prepared as a separate pre-mix, which, after being cooled, is subsequently incorporated with the other components of the shampoo composition. More specifically, the gel network component of the present invention may be prepared by heating the fatty alcohol, the secondary surfactant, and water to a level in the range of about 75° C. to about 90° C. and mixing. This mixture is cooled to a level in the range of about 27° C. to about 35° C. by, for example, passing the mixture through a heat exchanger. As a result of this cooling step, at least about fifty percent of the mixture of the fatty alcohol and the secondary surfactant crystallize to form a crystalline gel network.

Alternative methods of preparing the gel network component include sonication and/or milling of the fatty alcohol, the secondary surfactant, and water, while these components are heated, to reduce the particle size of the melted fatty alcohol phase. This results in an increase in surface area of the fatty alcohol phase, which allows the secondary surfactant and the water to swell the fatty alcohol phase. Another suitable variation in preparing the gel network includes heating and mixing the fatty alcohol and the secondary surfactant first, and then adding that mixture to the water.

Method of Use

The compositions of the present invention are used in a conventional manner for cleansing and conditioning hair or skin, including scalp, face, and body. Generally, a method of treating hair or skin of the present invention comprises applying the composition of the present invention to the hair or skin. More specifically, an effective amount of the composition is applied to the hair or skin, which has been wetted with water, and then the composition is rinsed off. Such effective amounts generally range from about 1 g to about 50 g, alternatively from about 1 g to about 20 g. Application to the hair typically includes working the composition through the hair such that most or all of the hair is contacted with the composition.

The method for treating the hair or skin comprises the steps of: (a) wetting the hair or skin with water; (b) applying an effective amount of the shampoo composition to the hair or skin, and (c) rinsing the applied areas of skin or hair with water. These steps can be repeated as many times as desired to achieve the desired cleansing and conditioning benefit.

In one embodiment, the shampoo composition of the present invention advantageously is used to treat damaged hair. Damaged hair may include hair selected from permed hair, oxidatively colored hair, and mechanically damaged hair.

In another embodiment, the shampoo composition is used to treat skin, such as the scalp, the face, and the body.

The shampoo compositions of this invention may be used as liquids, solids, semi-solids, flakes, gels, placed in a pressurized container with a propellant added, or used in a pump spray form. The viscosity of the product may be selected to accommodate the form desired.

Non-Limiting Examples

The shampoo compositions illustrated in the following Examples illustrate specific embodiments of the shampoo compositions of the present invention, but are not intended to be limiting thereof. Other modifications can be undertaken by the skilled artisan without departing from the spirit and scope of this invention. These exemplified embodiments of the shampoo composition of the present invention provide enhanced conditioning benefits to the hair.

The shampoo compositions illustrated in the following Examples are prepared by conventional formulation and mixing methods, an example of which is set forth below. All exemplified amounts are listed as weight percents and exclude minor materials such as diluents, preservatives, color solutions, imagery ingredients, botanicals, and so forth, unless otherwise specified. All percentages are based on weight unless otherwise specified.

Preparation of the Gel Network Pre-Mix

To prepare the gel network pre-mix, the water is heated to about 74° C. and the fatty alcohol and secondary surfactant (e.g. Sodium Laureth Sulfate) are added to it. After incorporation, this mixture is passed through a mill and heat exchanger where it is cooled to about 32° C. As a result of this cooling step, the fatty alcohol, the secondary surfactant, and the water form a crystalline gel Network Gel Network Pre-Mix Example Table of Gel Network Premix Example

| Premix | % |
| --- | --- |
| Sodium Laureth-1 Sulfate | 10.00 |
| Stearyl Alcohol | 7.07 |
| Cetyl Alcohol | 3.93 |
| Water | QS |

Preparation of Final Shampoo Compositions

The following examples illustrate the present invention. The exemplified compositions can be prepared by conventional formulation and mixing techniques. It will be appreciated that other modifications of the present invention within the skill of those in the hair care formulation art can be undertaken without departing from the spirit and scope of this invention. All parts, percentages, and ratios herein are by weight unless otherwise specified. Some components may come from suppliers as dilute solutions. The levels given reflect the weight percent of the active material, unless otherwise specified. A level of perfume and/or preservatives may also be included in the following examples.

Shampoo Composition Examples 1-74

| Example | 1 | 2 | 3 | 4 | 5 | 6 | 7 | 8 |
|---|---|---|---|---|---|---|---|---|
| Sodium Lauryl Sulfate | 7.19 | 7.42 | 6.96 | 6.96 | 5.60 | 5.82 | 6.51 | 7.19 |
| Sodium Laureth-1 Sulfate | 3.29 | 3.42 | 3.16 | 3.16 | 2.37 | 2.50 | 2.89 | 3.29 |
| Sodium Laureth Sulfate n > 1 | 3.53 | 3.67 | 3.38 | 3.38 | 2.54 | 2.68 | 3.10 | 3.53 |
| Cocamidopropyl betaine | 1.00 | 1.00 | 1.00 | 1.00 | 1.75 | 0.75 | 0.75 | 0.75 |
| Lauryl Hydroxysultain | 0.00 | 0.00 | 0.00 | 0.00 | 0.00 | 0.00 | 0.00 | 0.00 |
| Cocomonoethanolamide | 0.00 | 0.25 | 0.75 | 0.75 | 0.00 | 0.75 | 0.00 | 0.25 |
| Laureth-4 | 0.00 | 0.00 | 0.00 | 0.00 | 0.00 | 0.00 | 0.00 | 0.00 |
| Stearyl Alcohol | 0.96 | 0.77 | 0.64 | 1.29 | 0.64 | 0.96 | 0.77 | 0.64 |
| Cetyl Alcohol | 0.54 | 0.43 | 0.36 | 0.71 | 0.36 | 0.54 | 0.43 | 0.36 |
| Dimethicone 330M | 0.60 | 0.50 | 0.50 | 0.50 | 0.50 | 1.10 | 0.50 | 0.40 |
| Dimethicone | 0.00 | 0.00 | 0.00 | 0.00 | 0.00 | 0.00 | 0.00 | 0.00 |
| Guar Hydroxypropyltrimonium Chloride | 0.00 | 0.10 | 0.00 | 0.10 | 0.10 | 0.10 | 0.00 | 0.00 |
| Ethylene Glycol Distearate | 1.47 | 1.47 | 1.47 | 1.47 | 1.47 | 1.47 | 1.47 | 1.47 |
| Polyquaternium-76 | 0.15 | 0.00 | 0.10 | 0.00 | 0.00 | 0.10 | 0.00 | 0.00 |
| Polyquaternium-6 | 0.00 | 0.00 | 0.00 | 0.00 | 0.00 | 0.00 | 0.10 | 0.10 |
| Sodium Benzoate | 0.25 | 0.25 | 0.25 | 0.25 | 0.25 | 0.25 | 0.25 | 0.25 |
| Magnesium Sulfate | 0.00 | 0.00 | 0.00 | 0.00 | 0.00 | 0.00 | 0.00 | 0.00 |
| Water | QS | QS | QS | QS | QS | QS | QS | QS |
| Peak Melt Temperature | 25.96 | 26.31 | 25.17 | 28.64 | 27.38 | 36.92 | 24.25 | 25.67 |
| Enthalpy in J/g | 0.01 | 0.04 | 0.03 | 0.03 | 0.07 | 0.09 | 0.13 | 0.01 |
| Total Anionic | 14 | 14.5 | 13.5 | 13.5 | 10.5 | 11 | 12.5 | 14 |

| Example | 9 | 10 | 11 | 12 | 13 | 14 | 15 | 16 |
|---|---|---|---|---|---|---|---|---|
| Sodium Lauryl Sulfate | 7.64 | 6.28 | 6.28 | 4.69 | 7.64 | 7.19 | 5.82 | 6.96 |
| Sodium Laureth-1 Sulfate | 3.55 | 2.76 | 2.76 | 1.84 | 3.55 | 3.29 | 2.50 | 3.16 |
| Sodium Laureth Sulfate n > 1 | 3.81 | 2.96 | 2.96 | 1.97 | 3.81 | 3.53 | 2.68 | 3.38 |
| Cocamidopropyl betaine | 1.50 | 2.00 | 0.75 | 3.00 | 0.00 | 1.00 | 0.75 | 1.00 |
| Lauryl Hydroxysultain | 0.00 | 0.00 | 0.00 | 0.00 | 0.00 | 0.00 | 0.00 | 0.00 |
| Cocomonoethanolamide | 0.50 | 0.85 | 0.00 | 0.00 | 1.00 | 0.00 | 0.75 | 0.75 |
| Laureth-4 | 0.00 | 0.00 | 0.00 | 0.00 | 0.00 | 0.00 | 0.00 | 0.00 |
| Stearyl Alcohol | 0.64 | 0.64 | 0.96 | 1.16 | 0.64 | 0.90 | 0.96 | 0.96 |
| Cetyl Alcohol | 0.36 | 0.36 | 0.54 | 0.64 | 0.36 | 0.50 | 0.54 | 0.54 |
| Dimethicone 330M | 0.20 | 0.20 | 1.00 | 0.50 | 0.60 | 0.80 | 1.10 | 0.80 |
| Dimethicone | 0.00 | 0.00 | 0.00 | 0.00 | 0.00 | 0.00 | 0.00 | 0.00 |
| Guar Hydroxypropyltrimonium Chloride | 0.00 | 0.00 | 0.10 | 0.10 | 0.10 | 0.10 | 0.10 | 0.10 |

-continued

| | | | | | | | | |
|---|---|---|---|---|---|---|---|---|
| Ethylene Glycol Distearate | 1.47 | 1.47 | 1.47 | 1.47 | 1.47 | 1.47 | 1.47 | 1.47 |
| Polyquaternium-76 | 0.10 | 0.10 | 0.00 | 0.10 | 0.10 | 0.10 | 0.10 | 0.10 |
| Polyquaternium-6 | 0.00 | 0.00 | 0.00 | 0.00 | 0.00 | 0.00 | 0.00 | 0.00 |
| Sodium Benzoate | 0.25 | 0.25 | 0.25 | 0.25 | 0.25 | 0.25 | 0.25 | 0.25 |
| Magnesium Sulfate | 0.00 | 0.00 | 0.00 | 0.00 | 0.00 | 0.00 | 0.00 | 0.00 |
| Water | QS | QS | QS | QS | QS | QS | QS | QS |
| Peak Melt Temperature | 24.09 | 25.63 | 29.13 | . | 24.12 | 29.38 | 26.92 | 25.68 |
| Enthalpy in J/g | 0.004 | 0.02 | 0.17 | 0.00 | 0.02 | 0.0 | 0.09 | 0.03 |
| Total Anionic | 15 | 12 | 12 | 8.5 | 15 | 14 | 11 | 13.5 |

| Example | 17 | 18 | 19 | 20 | 21 | 22 | 23 | 24 |
|---|---|---|---|---|---|---|---|---|
| Sodium Lauryl Sulfate | 5.82 | 6.96 | 6.28 | 7.64 | 7.60 | 6.45 | 8.12 | 8.54 |
| Sodium Laureth-1 Sulfate | 2.50 | 3.16 | 2.76 | 3.55 | 2.56 | 2.49 | 2.93 | 3.36 |
| Sodium Laureth Sulfate n > 1 | 2.68 | 3.38 | 2.96 | 3.81 | 2.75 | 2.66 | 3.14 | 3.60 |
| Cocamidopropyl betaine | 2.00 | 1.00 | 0.75 | 1.50 | 3.06 | 1.73 | 0.00 | 1.15 |
| Lauryl Hydroxysultain | 0.00 | 0.00 | 0.00 | 0.00 | 0.00 | 0.00 | 0.00 | 0.00 |
| Cocomonoethanolamide | 0.00 | 0.75 | 0.00 | 0.50 | 0.00 | 0.67 | 1.00 | 1.00 |
| Laureth-4 | 0.00 | 0.00 | 0.00 | 0.00 | 0.33 | 0.67 | 0.67 | 0.00 |
| Stearyl Alcohol | 0.64 | 0.64 | 1.29 | 0.77 | 1.29 | 0.64 | 1.61 | 0.96 |
| Cetyl Alcohol | 0.36 | 0.36 | 0.71 | 0.43 | 0.71 | 0.36 | 0.89 | 0.54 |
| Dimethicone 330M | 0.80 | 0.80 | 0.60 | 1.00 | 0.70 | 0.70 | 0.70 | 0.70 |
| Dimethicone | 0.00 | 0.00 | 0.00 | 0.00 | 0.00 | 0.00 | 0.00 | 0.00 |
| Guar Hydroxypropyltrimonium Chloride | 0.10 | 0.10 | 0.10 | 0.10 | 0.10 | 0.10 | 0.10 | 0.10 |
| Ethylene Glycol Distearate | 1.47 | 1.47 | 1.47 | 1.47 | 1.47 | 1.47 | 1.47 | 1.47 |
| Polyquaternium-76 | 0.00 | 0.00 | 0.00 | 0.00 | 0.00 | 0.00 | 0.00 | 0.00 |
| Polyquaternium-6 | 0.10 | 0.10 | 0.10 | 0.10 | 0.00 | 0.00 | 0.00 | 0.00 |
| Sodium Benzoate | 0.25 | 0.25 | 0.25 | 0.25 | 0.25 | 0.25 | 0.25 | 0.25 |
| Magnesium Sulfate | 0.00 | 0.00 | 0.00 | 0.00 | 0.00 | 0.00 | 0.00 | 0.00 |
| Water | QS | QS | QS | QS | QS | QS | QS | QS |
| Peak Melt Temperature | . | . | 25.24 | 24.66 | 26.96 | 24.95 | 26.6 | 25.78 |
| Enthalpy in J/g | 0.00 | 0.00 | 0.01 | 0.09 | 0.10 | 0.17 | 0.19 | 0.11 |
| Total Anionic | 11 | 13.5 | 12 | 15 | 12.91 | 11.6 | 14.2 | 15.5 |

| Example | 25 | 26 | 27 | 28 | 29 | 30 | 31 | 32 |
|---|---|---|---|---|---|---|---|---|
| Sodium Lauryl Sulfate | 5.32 | 8.62 | 5.25 | 8.38 | 5.63 | 5.73 | 8.62 | 6.14 |
| Sodium Laureth-1 Sulfate | 1.78 | 3.32 | 1.82 | 3.12 | 1.63 | 1.58 | 3.32 | 2.63 |
| Sodium Laureth Sulfate n > 1 | 1.90 | 3.56 | 1.95 | 3.35 | 1.74 | 1.69 | 3.56 | 2.82 |
| Cocamidopropyl betaine | 0.00 | 0.00 | 0.70 | 0.00 | 0.00 | 1.54 | 2.32 | 2.48 |
| Lauryl Hydroxysultain | 0.00 | 0.00 | 0.00 | 0.00 | 0.00 | 0.00 | 0.00 | 0.00 |

-continued

| | | | | | | | | |
|---|---|---|---|---|---|---|---|---|
| Cocomono-ethanolamide | 1.00 | 0.00 | 0.67 | 0.33 | 0.67 | 0.67 | 0.67 | 1.00 |
| Laureth-4 | 0.67 | 0.67 | 0.67 | 0.00 | 1.00 | 0.33 | 0.33 | 0.00 |
| Stearyl Alcohol | 0.64 | 0.96 | 0.64 | 1.29 | 1.29 | 1.61 | 0.64 | 0.64 |
| Cetyl Alcohol | 0.36 | 0.54 | 0.36 | 0.71 | 0.71 | 0.89 | 0.36 | 0.36 |
| Dimethicone 330M | 0.70 | 0.70 | 0.70 | 0.70 | 0.70 | 0.70 | 0.70 | 0.70 |
| Dimethicone | 0.00 | 0.00 | 0.00 | 0.00 | 0.00 | 0.00 | 0.00 | 0.00 |
| Guar Hydroxy-propyl-trimonium Chloride | 0.10 | 0.10 | 0.10 | 0.10 | 0.10 | 0.10 | 0.10 | 0.10 |
| Ethylene Glycol Distearate | 1.47 | 1.47 | 1.47 | 1.47 | 1.47 | 1.47 | 1.47 | 1.47 |
| Polyquater-nium-76 | 0.00 | 0.00 | 0.00 | 0.00 | 0.00 | 0.00 | 0.00 | 0.00 |
| Polyquater-nium-6 | 0.00 | 0.00 | 0.00 | 0.00 | 0.00 | 0.00 | 0.00 | 0.00 |
| Sodium Benzoate | 0.25 | 0.25 | 0.42 | 0.25 | 0.25 | 0.25 | 0.25 | 0.25 |
| Magnesium Sulfate | 0.00 | 0.00 | 0.00 | 0.50 | 0.00 | 0.00 | 0.00 | 0.00 |
| Water | QS | QS | QS | QS | QS | QS | QS | QS |
| Peak Melt Temperature | 26.26 | 26.80 | 26.93 | 27.17 | . | . | 23.39 | 25.13 |
| Enthalpy in J/g | 0.16 | 0.12 | 0.16 | 0.13 | 0.00 | 0.00 | 0.03 | 0.08 |
| Total Anionic | 9 | 15.5 | 9.02 | 14.85 | 9 | 9.01 | 15.5 | 11.6 |

| Example | 33 | 34 | 35 | 36 | 37 | 38 | 39 | 40 |
|---|---|---|---|---|---|---|---|---|
| Sodium Lauryl Sulfate | 5.37 | 5.57 | 5.40 | 5.32 | 6.69 | 8.54 | 6.68 | 6.83 |
| Sodium Laureth-1 Sulfate | 1.75 | 1.66 | 1.74 | 1.78 | 2.69 | 3.36 | 2.69 | 2.61 |
| Sodium Laureth Sulfate n > 1 | 1.88 | 1.78 | 1.86 | 1.90 | 2.88 | 3.60 | 2.88 | 2.80 |
| Cocamido-propyl betaine | 2.16 | 2.24 | 2.17 | 0.71 | 1.80 | 2.29 | 0.00 | 1.84 |
| Lauryl Hydroxy-sultain | 0.00 | 0.00 | 0.00 | 0.00 | 0.00 | 0.00 | 0.00 | 0.00 |
| Cocomono-ethanolamide | 0.00 | 0.00 | 1.00 | 0.33 | 0.33 | 0.33 | 0.67 | 0.67 |
| Laureth-4 | 1.00 | 0.00 | 0.00 | 0.33 | 0.33 | 0.00 | 0.00 | 0.67 |
| Stearyl Alcohol | 1.61 | 0.64 | 1.61 | 0.96 | 0.96 | 1,.61 | 1.61 | 0.96 |
| Cetyl Alcohol | 0.89 | 0.36 | 0.89 | 0.54 | 0.54 | 0.89 | 0.89 | 0.54 |
| Dimethicone 330M | 0.70 | 0.70 | 0.70 | 0.70 | 0.70 | 0.70 | 0.70 | 0.70 |
| Dimethicone | 0.00 | 0.00 | 0.00 | 0.00 | 0.00 | 0.00 | 0.00 | 0.00 |
| Guar Hydroxy-propyl-trimonium Chloride | 0.10 | 0.10 | 0.10 | 0.10 | 0.10 | 0.10 | 0.10 | 0.10 |
| Ethylene Glycol Distearate | 1.47 | 1.47 | 1.47 | 1.47 | 1.47 | 1.47 | 1.47 | 1.47 |
| Polyquater-nium-76 | 0.00 | 0.00 | 0.00 | 0.00 | 0.00 | 0.00 | 0.00 | 0.00 |
| Polyquater-nium-6 | 0.00 | 0.00 | 0.00 | 0.00 | 0.00 | 0.00 | 0.00 | 0.00 |
| Sodium Benzoate | 0.25 | 0.25 | 0.25 | 0.25 | 0.25 | 0.25 | 0.25 | 0.25 |
| Magnesium Sulfate | 0.00 | 0.00 | 0.00 | 0.00 | 0.00 | 0.00 | 0.00 | 0.00 |
| Water | QS | QS | QS | QS | QS | QS | QS | QS |
| Peak Melt Temperature | . | 27.72 | . | . | 27.88 | 27.86 | . | 27.11 |
| Enthalpy in J/g | 0.00 | 0.05 | 0.00 | 0.00 | 0.03 | 0.02 | 0.00 | 0.08 |
| Total Anionic | 9 | 9 | 9 | 9 | 12.25 | 15.5 | 12.25 | 12.25 |

-continued

| Example | 41 | 42 | 43 | 44 | 45 | 46 | 47 | 48 |
|---|---|---|---|---|---|---|---|---|
| Sodium Lauryl Sulfate | 8.38 | 5.54 | 5.86 | 6.67 | 6.00 | 7.64 | 5.73 | 6.05 |
| Sodium Laureth-1 Sulfate | 3.12 | 2.30 | 2.14 | 2.88 | 2.50 | 2.64 | 1.58 | 2.58 |
| Sodium Laureth Sulfate n > 1 | 3.35 | 2.46 | 2.30 | 3.09 | 2.68 | 2.83 | 1.69 | 2.76 |
| Cocamido-propyl betaine | 1.12 | 0.00 | 0.79 | 0.90 | 0.00 | 3.08 | 1.54 | 2.44 |
| Lauryl Hydroxy-sultain | 0.00 | 0.00 | 0.00 | 0.00 | 0.00 | 0.00 | 0.00 | 0.00 |
| Cocomono-ethanolamide | 0.00 | 0.00 | 1.00 | 0.33 | 1.00 | 1.00 | 0.00 | 0.00 |
| Laureth-4 | 1.00 | 0.67 | 0.67 | 0.00 | 1.00 | 0.33 | 0.67 | 0.33 |
| Stearyl Alcohol | 0.96 | 0.96 | 1.61 | 0.96 | 1.61 | 1.29 | 1.61 | 1.61 |
| Cetyl Alcohol | 0.54 | 0.54 | 0.89 | 0.54 | 0.89 | 0.71 | 0.89 | 0.89 |
| Dimethicone 330M | 0.70 | 0.70 | 0.70 | 0.70 | 0.70 | 0.70 | 0.70 | 0.70 |
| Dimethicone | 0.00 | 0.00 | 0.00 | 0.00 | 0.00 | 0.00 | 0.00 | 0.00 |
| Guar Hydroxy-propyl-trimonium Chloride | 0.10 | 0.10 | 0.10 | 0.10 | 0.10 | 0.10 | 0.10 | 0.10 |
| Ethylene Glycol Distearate | 1.47 | 1.47 | 1.47 | 1.47 | 1.47 | 1.47 | 1.47 | 1.47 |
| Polyquater-nium-76 | 0.00 | 0.00 | 0.00 | 0.00 | 0.00 | 0.00 | 0.00 | 0.00 |
| Polyquater-nium-6 | 0.00 | 0.00 | 0.00 | 0.00 | 0.00 | 0.00 | 0.00 | 0.00 |
| Sodium Benzoate | 0.50 | 0.50 | 0.33 | 0.33 | 0.50 | 0.42 | 0.50 | 0.25 |
| Magnesium Sulfate | 0.00 | 0.17 | 0.33 | 0.33 | 0.00 | 0.50 | 0.50 | 0.50 |
| Water | QS | QS | QS | QS | QS | QS | QS | QS |
| Peak Melt Temperature | 27.46 | . | . | 27.31 | . | . | . | . |
| Enthalpy in J/g | 0.07 | 0.00 | 0.00 | 0.07 | 0.00 | 0.00 | 0.00 | 0.00 |
| Total Anionic | 14.85 | 10.3 | 10.3 | 12.63 | 11.17 | 13.11 | 9 | 11.39 |

| Example | 49 | 50 | 51 | 52 | 53 | 54 | 55 | 56 |
|---|---|---|---|---|---|---|---|---|
| Sodium Lauryl Sulfate | 5.12 | 5.16 | 5.73 | 8.23 | 6.24 | 5.59 | 6.96 | 6.96 |
| Sodium Laureth-1 Sulfate | 1.88 | 1.85 | 1.58 | 3.51 | 2.63 | 1.66 | 3.16 | 3.16 |
| Sodium Laureth Sulfate n > 1 | 2.01 | 1.99 | 1.69 | 3.76 | 2.82 | 1.78 | 3.38 | 3.38 |
| Cocamido-propyl betaine | 2.06 | 0.00 | 1.54 | 2.21 | 2.52 | 0.75 | 1.00 | 0.00 |
| Lauryl Hydroxy-sultain | 0.00 | 0.00 | 0.00 | 0.00 | 0.00 | 0.00 | 0.00 | 1.00 |
| Cocomono-ethanolamide | 0.67 | 0.00 | 0.67 | 0.00 | 0.00 | 0.33 | 0.75 | 0.75 |
| Laureth-4 | 1.00 | 0.67 | 1.00 | 0.00 | 0.33 | 0.00 | 0.00 | 0.00 |
| Stearyl Alcohol | 0.96 | 0.64 | 1.29 | 0.64 | 1.61 | 1.29 | 1.29 | 1.29 |
| Cetyl Alcohol | 0.54 | 0.36 | 0.71 | 0.36 | 0.89 | 0.71 | 0.71 | 0.71 |
| Dimethicone 330M | 0.70 | 0.70 | 0.70 | 0.70 | 0.70 | 0.70 | 0.00 | 0.50 |
| Dimethicone | 0.00 | 0.00 | 0.00 | 0.00 | 0.00 | 0.00 | 0.80 | 0.00 |
| Guar Hydroxy-propyl-trimonium Chloride | 0.10 | 0.10 | 0.10 | 0.10 | 0.10 | 0.10 | 0.10 | 0.10 |
| Ethylene Glycol Distearate | 1.47 | 1.47 | 1.47 | 1.47 | 1.47 | 1.47 | 1.47 | 1.47 |

-continued

| | | | | | | | | |
|---|---|---|---|---|---|---|---|---|
| Polyquaternium-76 | 0.00 | 0.00 | 0.00 | 0.00 | 0.00 | 0.00 | 0.00 | 0.00 |
| Polyquaternium-6 | 0.00 | 0.00 | 0.00 | 0.00 | 0.00 | 0.00 | 0.00 | 0.00 |
| Sodium Benzoate | 0.50 | 0.33 | 0.25 | 0.00 | 0.42 | 0.50 | 0.25 | 0.25 |
| Magnesium Sulfate | 0.17 | 0.50 | 0.17 | 0.50 | 0.00 | 0.33 | 0.00 | 0.00 |
| Water | QS | QS | QS | QS | QS | QS | QS | QS |
| Peak Melt Temperature | . | . | . | . | . | . | 24.51 | 28.6 |
| Enthalpy in J/g | 0.00 | 0.00 | 0.00 | 0.00 | 0.00 | 0.00 | 0.07 | 0.08 |
| Total Anionic | 9.01 | 9 | 9 | 15.5 | 11.69 | 9.03 | 13.5 | 13.5 |

| Example | 57 | 58 | 59 | 60 | 61 | 62 | 63 | 64 |
|---|---|---|---|---|---|---|---|---|
| Sodium Lauryl Sulfate | 4.09844 | 4.09844 | 4.09844 | 4.09844 | 4.09844 | 4.09844 | 4.938539 | 4.938539 |
| Sodium Laureth-1 Sulfate | 2.368988 | 2.368988 | 2.368988 | 2.368988 | 2.368988 | 2.368988 | 2.854584 | 2.854584 |
| Sodium Laureth Sulfate n > 1 | 2.540132 | 2.540132 | 2.540132 | 2.540132 | 2.540132 | 2.540132 | 3.060809 | 3.060809 |
| Cocamidopropyl betaine | 0.6924 | 0.6924 | 0.6924 | 0.6924 | 0.6924 | 0.6924 | 0.846257 | 0.846257 |
| Cocomonoethanolamide | 0.75 | 0.75 | 0.75 | 0.75 | 0.75 | 0.75 | 0.75 | 0.75 |
| Stearyl Alcohol | 1.28 | 1.28 | 1.28 | 1.28 | 1.28 | 1.28 | 1.28 | 1.28 |
| Cetyl Alcohol | 0.71 | 0.71 | 0.71 | 0.71 | 0.71 | 0.71 | 0.71 | 0.71 |
| Guar Hydroxypropyltrimonium Chloride | 0.15 | 0.15 | 0.15 | 0.15 | 0.15 | 0.15 | 0.15 | 0.15 |
| Ethylene Glycol Distearate | 1.47 | 1.47 | 1.47 | 1.47 | 1.47 | 1.47 | 1.47 | 1.47 |
| Sodium Benzoate | 0.25 | 0.25 | 0.25 | 0.25 | 0.25 | 0.25 | 0.25 | 0.25 |
| EDTA | 0.155 | 0.155 | 0.155 | 0.155 | 0.155 | 0.155 | 0.155 | 0.155 |
| Dimethicone 330M | 0.8001 | 0.8001 | 0.8001 | 0.8001 | 0.8001 | 0.8001 | 0.8001 | 0.8001 |
| Citric Acid | 0.128571 | 0.128571 | 0.128571 | 0.128571 | 0.128571 | 0.128571 | 0.128571 | 0.128571 |
| Sodium Chloride | 1.2 | 1.3 | 9.8 | 11.2 | 11.9 | 12.6 | 1.1 | 1.2 |
| Water | QS | QS | QS | QS | QS | QS | QS | QS |
| Frequency of Crossover | 3.369 | 3.143 | 69.53 | 4.222 | 84.28 | 15.97 | 4.333 | 2.563 |
| Zero Shear Visc | 8041 | 7448 | 10770 | 9162 | 7812 | 11130 | 6135 | 7913 |

| Example | 65 | 66 | 67 | 68 | 69 | 70 | 71 | 72 |
|---|---|---|---|---|---|---|---|---|
| Sodium Lauryl Sulfate | 4.938539 | 4.938539 | 5.778469 | 5.778469 | 5.778469 | 5.778469 | 5.778469 | 5.778469 |
| Sodium Laureth-1 Sulfate | 2.854584 | 2.854584 | 3.340082 | 3.340082 | 3.340082 | 3.340082 | 3.340082 | 3.340082 |
| Sodium Laureth Sulfate n > 1 | 3.060809 | 3.060809 | 3.581381 | 3.581381 | 3.581381 | 3.581381 | 3.581381 | 3.581381 |
| Cocamidopropyl betaine | 0.846257 | 0.846257 | 1.000114 | 1.000114 | 1.000114 | 1.000114 | 1.000114 | 1.000114 |
| Cocomonoethanolamide | 0.75 | 0.75 | 0.75 | 0.75 | 0.75 | 0.75 | 0.75 | 0.75 |
| Stearyl Alcohol | 1.28 | 1.28 | 1.28 | 1.28 | 1.28 | 1.28 | 1.28 | 1.28 |
| Cetyl Alcohol | 0.71 | 0.71 | 0.71 | 0.71 | 0.71 | 0.71 | 0.71 | 0.71 |
| Guar Hydroxypropyltrimonium Chloride | 0.15 | 0.15 | 0.15 | 0.15 | 0.15 | 0.15 | 0.15 | 0.15 |
| Ethylene Glycol Distearate | 1.47 | 1.47 | 1.47 | 1.47 | 1.47 | 1.47 | 1.47 | 1.47 |

-continued

| | | | | | | | | |
|---|---|---|---|---|---|---|---|---|
| Sodium Benzoate | 0.25 | 0.25 | 0.25 | 0.25 | 0.25 | 0.25 | 0.25 | 0.25 |
| EDTA | 0.155 | 0.155 | 0.155 | 0.155 | 0.155 | 0.155 | 0.155 | 0.155 |
| Dimethicone 330M | 0.8001 | 0.8001 | 0.8001 | 0.8001 | 0.8001 | 0.8001 | 0.8001 | 0.8001 |
| Citric Acid | 0.128571 | 0.128571 | 0.157143 | 0.157143 | 0.157143 | 0.157143 | 0.157143 | 0.157143 |
| Sodium Chloride | 1.3 | 1.8 | 0.8 | 0.9 | 1 | 1.1 | 1.2 | 1.8 |
| Water | QS | QS | QS | QS | QS | QS | QS | QS |
| Frequency of Crossover | 3.7 | 89.52 | 13.11 | 5.529 | 3.157 | 2.1 | 37.41 | 6.071 |
| Zero Shear Visc | 12030 | 14680 | 6792 | 6853 | 9012 | 13080 | 18700 | 22090 |

| Ingredient | Supplied As |
|---|---|
| Polyquaternium-76 | Polyquaternium-76 10% active from Rhodia |
| Polyquaternium-6 | Mirapol 100S from Rhodia |
| Jaguar C17 | Jaguar C17 from Rhodia |
| Guar 3196 | N-Hance 3196 from Hercules Aqualon Div |
| C500 | Jaguar C500 from Rhodia |
| Dimethicone 330M | Dimethicone 330M from Momentive |
| Dimethicone | Besil DM500 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A shampoo composition comprising:
   a. a dispersed gel network phase comprising:
      i. at least 0.05% of one or more fatty alcohols, by weight of said shampoo composition;
      ii. at least 0.01% of one or more secondary surfactants by weight of said shampoo composition selected from the group consisting of anionic surfactants, cationic surfactants, non-ionic surfactants and mixtures thereof; and
      iii. water; and
   b. from about 5% to about 50% of a combination of sodium lauryl sulfate and sodium laureth-n sulfate;
   c. less than 3.82% of sodium laureth-n sulfate having n>1;
   d. greater than 0.5% sodium laureth-1 sulfate;
   e. from about 0.5% to about 3% of a co-surfactant selected from the group consisting of amphoteric, zwitterionic, and nonionic surfactants, by weight of said shampoo composition;
   f. at least 20% of an aqueous carrier, by weight of said shampoo composition;
   wherein said shampoo composition has an enthalpy of transition from about 0 J/g to about 0.2 J/g as measured according to differential scanning calorimetry in a peak melt transition temperature range between about 18° C. to about 30° C.

2. The shampoo composition according to claim 1, wherein said shampoo composition comprises from about 10% to about 17% of said combination of sodium lauryl sulfate and sodium laureth-n sulfate.

3. The shampoo composition according to claim 1, wherein said shampoo composition comprises from about 0.5% to about 2% of a co-surfactant selected from the group consisting of amphoteric, zwitterionic, and nonionic surfactants, by weight of said shampoo composition.

4. The shampoo composition according to claim 1, wherein said shampoo composition comprises from about 0.5% to about 1.75% of a co-surfactant selected from the group consisting of amphoteric, zwitterionic, and nonionic surfactants, by weight of said shampoo composition.

5. The shampoo composition according to claim 1, wherein said shampoo composition comprises from about 4% to about 9% sodium lauryl sulfate, by weight of said shampoo composition.

6. The shampoo composition according to claim 1, wherein said shampoo composition comprises from 0.5% to about 5% sodium laureth-1 sulfate, by weight of said shampoo composition.

7. The shampoo composition according to claim 1, wherein said dispersed gel network phase comprises from about 0.05% to about 14% of one or more fatty alcohols by weight of said shampoo composition.

8. The shampoo composition according to claim 1, wherein said one or more fatty alcohols is selected from the group consisting of cetyl alcohol, stearyl alcohol, behenyl alcohol, and mixtures thereof.

9. The shampoo composition according to claim 1, wherein said dispersed gel network phase comprises from about 0.2% to about 5% of one or more secondary surfactants by weight of said shampoo composition.

10. The shampoo composition according to claim 1, wherein said secondary surfactant is selected from the group consisting of anionic surfactants, cationic surfactants, nonionic surfactants and mixtures thereof.

11. The shampoo composition according to claim 1, wherein said secondary surfactant is selected from the group consisting of cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, and mixtures thereof.

12. The shampoo composition according to claim 1, wherein said secondary surfactant is selected from the group consisting of ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate, and mixtures thereof.

13. The shampoo composition according to claim 1, wherein said shampoo composition has an enthalpy of transition from about 0 J/g to about 0.1 J/g as measured according to differential scanning calorimetry in a peak melt transition temperature range between about 18° C. to about 30° C.

14. The shampoo composition according to claim 1, wherein said dispersed gel network phase further comprises one or more fatty compounds selected from the group consisting of fatty amides, di-fatty ethers, fatty carbamates, fatty acids, fatty esters, fatty phosphorous compounds, fatty sorbitan derivatives, alkyl sulfoxides, and mixtures thereof.

15. The shampoo composition according to claim 1, wherein said zwitterionic surfactant is a betaine.

16. The shampoo composition according to claim 1, wherein said zwitterionic surfactant is a sultaine.

17. The shampoo composition according to claim 1, wherein said nonionic surfactant is a cocomonethanolamine.

18. The shampoo composition according to claim 1, wherein said shampoo composition has:
   a. a zero shear viscosity between about 1,000 cps to about 30,000 cps; and
   b. a frequency at a crossover point greater than 2 Hz.

19. A process for preparing the shampoo composition according to claim 1, said process comprising the steps of:
   a. combining a fatty alcohol and a surfactant in a weight ratio of fatty alcohol to surfactant of about 1:1 to about 40:1 and at a temperature sufficient to allow partitioning of the surfactant into the fatty alcohol to form a premix;
   b. cooling the premix below the chain melt temperature of the fatty alcohol to form a solid crystalline gel network; and
   c. adding the solid crystalline gel network to a detersive surfactant and an aqueous carrier to form a shampoo composition.

20. A shampoo composition comprising:
   a. a dispersed gel network phase comprising:
      i. at least 0.05% of one or more fatty alcohols, by weight of said shampoo composition;
      ii. at least 0.01% of one or more secondary surfactants by weight of said shampoo composition selected from the group consisting of anionic surfactants, cationic surfactants, non-ionic surfactants and mixtures thereof; and
      iii. water; and
   b. from about 5% to about 50% of a combination of sodium lauryl sulfate and sodium laureth-n sulfate;
   c. less than 3.82% of sodium laureth-n sulfate having n>1;
   d. greater than 0.5% sodium laureth-1 sulfate;
   e. from about 0.5% to about 3% of a co-surfactant selected from the group consisting of amphoteric, zwitterionic, and nonionic surfactants, by weight of said shampoo composition;
   f. at least 20% of an aqueous carrier, by weight of said shampoo composition;
wherein said shampoo composition has an enthalpy of transition from about 0 J/g to about 0.2 J/g as measured according to differential scanning calorimetry in a peak melt transition temperature range between about 18° C. to about 30° C.; and wherein said shampoo composition has a zero shear viscosity between about 1,000 cps to about 30,000 cps, and a frequency at a crossover point greater than 2 Hz.

* * * * *